US010077246B2

(12) United States Patent
Johansson et al.

(10) Patent No.: US 10,077,246 B2
(45) Date of Patent: Sep. 18, 2018

(54) TRICYCLIC PRODRUGS

(71) Applicant: Glactone Pharma Development AB, Helsingborg (SE)

(72) Inventors: Martin Johansson, Peterborough (CA); Olov Sterner, Malmö (SE)

(73) Assignee: Glactone Pharma Development AB, Helsingborg (SE)

( * ) Notice: Subject to any disclaimer, the term of this patent is extended or adjusted under 35 U.S.C. 154(b) by 0 days.

(21) Appl. No.: 15/124,096

(22) PCT Filed: Mar. 6, 2015

(86) PCT No.: PCT/EP2015/054754
§ 371 (c)(1),
(2) Date: Sep. 7, 2016

(87) PCT Pub. No.: WO2015/132396
PCT Pub. Date: Sep. 11, 2015

(65) Prior Publication Data
US 2017/0015644 A1 Jan. 19, 2017

(30) Foreign Application Priority Data
Mar. 7, 2014 (SE) ..................... 1450263

(51) Int. Cl.
*C07D 307/93* (2006.01)
*A61K 31/365* (2006.01)
*A61K 38/05* (2006.01)
*A61K 38/06* (2006.01)
*C07K 5/02* (2006.01)
*C07K 5/062* (2006.01)

(52) U.S. Cl.
CPC .......... *C07D 307/93* (2013.01); *A61K 31/365* (2013.01); *A61K 38/05* (2013.01); *A61K 38/063* (2013.01); *C07K 5/0215* (2013.01); *C07K 5/06052* (2013.01)

(58) Field of Classification Search
CPC ............................ C07D 307/93; A61K 31/365
See application file for complete search history.

(56) References Cited

U.S. PATENT DOCUMENTS 6,512,007 B1 1/2003 Baumgarten et al.
2013/0310451 A1 11/2013 Gidloef et al.

FOREIGN PATENT DOCUMENTS

WO 2012010555 A1 1/2012
WO 2012011864 A1 1/2012

OTHER PUBLICATIONS

International Search Report and Written Opinion issued by the European Patent Office acting as the International Searching Authority for International Patent Application No. PCT/EP2015/054754, dated Jun. 17, 2015 (16 pages).
Johnston et al., "STAT3 Signaling: Anticancer Strategies and Challenges," Molecular Interventions, Feb. 2011, pp. 18-26, vol. 11, Iss. 1, Pittsburgh, PA, USA.
Sansone et al., "Targeting the Interleukin-6/Jak/Stat Pathway in Human Malignancies," Journal of Clinical Oncology, Feb. 21, 2012, pp. 1-10, American Society of Clinical Oncology, online http://jco.ascopubs.org/cgi/doi/10.1200/JCO.2010.31.8907.
Miklossy et al., "Therapeutic Modulators of STAT Signalling for Human Diseases," Nature Reviews Drug Discovery, Aug. 2013, pp. 611-629, vol. 12, Macmillan Publishers Ltd.
Yu et al., "Revisiting STAT3 Signalling in Cancer: New and Unexpected Biological Functions," Nature Reviews Cancer, Nov. 2014, pp. 736-746, vol. 14, Macmillan Publishers Ltd.
Weidler et al., "Inhibition of Interleukin-6 Signaling by Galiellalactone," FEBS Letters, Oct. 27, 2000, pp. 1-6, vol. 484, Iss. 1, http://dx.doi.org/10.1016/S0014-5793(00)02115-3.
Hellsten et al., "Galiellalactone is a Novel Therapeutic Candidate Against Hormon-Refractory Prostate Cancer Expressing Activated Stat3," Wiley InterScience, 2008, pp. 269-280, vol. 68, Wiley-Liss, Inc.
Don-Doncow et al., "Galliellalactone Is a Direct Inhibitor of the Transcription Factor STAT3 in Prostate Cancer Cells," Journal of Biological Chemistry, Jun. 6, 2014, pp. 15969-15978, vol. 289, No. 23, The American Society of Biochemistry and Molecular Biology, Inc., USA.
Nussbaum et al., "The High-Intrinsic Diels-Alder Reactivity of (-)-Galiellalactone; Generating Four Quaternary Carbon Centers under Mild Conditions," Eur. J. Or. Chem., 2008, pp. 2783-2790, Wiley-VCH Verlag GmbH & Co. KGaA, Weinheim.

(Continued)

*Primary Examiner* — Samira Jean-Louis
(74) *Attorney, Agent, or Firm* — Honigman Miller Schwartz and Cohn LLP

(57) ABSTRACT

Prodrugs (I) and (Ia) of galiellactone, and derivatives thereof, are provided by reacting the parent compound, e.g. galiellactone, with a thiol. Such drugs may be administered orally to treat cancer and other proliferative diseases.

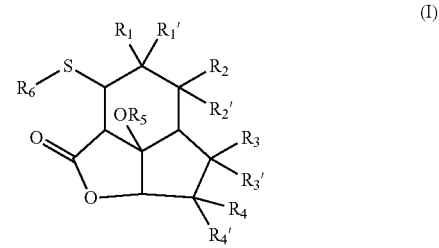

(I)

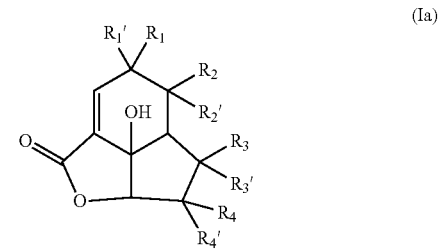

(Ia)

15 Claims, No Drawings

(56) References Cited

OTHER PUBLICATIONS

Woods et al., "Amino-Derivatives of the Sesquiterpene Lactone Class of Natural Products as Prodrugs," Med. Chem. Commun., 2013, pp. 27-33, vol. 4, The Royal Society of Chemistry.
Neelakantan et al., "Aminoparthenolides as Novel Anti-Leukemic Agents: Discovery of the NF-κb Inhibitor, DMAPT (LC-1)," Bioorganic & Medicinal Chemistry Letters, 2009, pp. 4346-4349, vol. 19, Elsevier Ltd., USA.
Rudolph et al., "Inhibition of TGF-β Signaling by the Fungal Lactones (S)-Curvularin, Dehydrocurvularin, Oxacyclododecindione and Galeiellalactone," Cytokine, Jan. 2013, pp. 285-296, vol. 61, No. 1, Elsevier Ltd., USA.
Hausding et al., "Induction of Tolerogenic Lung CD4+ T Cells by Local Treatment with a pSTAT-3 and pSTAT-5 Inhibitor Ameliorated Experimental Allergic Asthma," International Immunology, Jan. 2011, pp. 1-15, vol. 23, No. 1, The Japanese Society for Immunology.
Rayner, Christopher M., "Synthesis of Thiols, Sulfides, Sulfoxides and Sulfones," Contemporary Organic Synthesis, 1995, pp. 409-440, vol. 2.
Gidlöf et al., "Tandem Pd-Catalyzed Carbonylation and Intramolecular Vinyl Allene Diels-Alder Reaction toward Galiellalactone Analogues," Organic Letters, 2010, pp. 5100-5103, vol. 12, No. 22, American Chemical Society.
Johansson et al., Synthesis of (-)-Galiellalactone, The Journal of Antibiotics, Jul. 2002, pp. 663-665, vol. 55, No. 7, Lund University, Lund, SE.
Köpkcke et al., "Galiellalactone and its Biogenitc Precursors as Chemotaxonomin Markers of the Sarcosomataceae (Ascomycota)," Phytochemistry, 2002, pp. 709-714, vol. 60, Elsevier Science Ltd.
Johansson, "Biosynthetic and Synthetic Studies of the Fungal Metabolite Galiellalactone," Lund Institute of Technology, 2002, Lund University, SE.
Lai et al., "A STAT Inhibitor Patent Review: Progress Since 2011," Expert Opin. Ther. Patents, Sep. 22, 2015, pp. 1-25, vol. 25, No. 12, Informa US, Ltd.
Lavecchia et al., "Novel Inhibitors of Signal Transducer and Activator of Transcription 3 Signaling Pathway: An Update on the Recent Patent Literature," Expert Opin. Ther. Patents, 2014, pp. 1-18, vol. 4, No. 4, Informa US, Ltd.
Santoni et al., "Investigational Therapies Targeting Signal Transducer and Activator of Transcription 3 for the Treatment of Cancer," Expert Opin. Ther. Patents, 2015, pp. 1-16, vol. 24, No. 6, Informa US, Ltd.

this paragraph intentionally reconstructed from visible text …

TRICYCLIC PRODRUGS

This application is a 35 U.S.C. § 371 United States national stage application of International Application No. PCT/EP2015/054754, filed Mar. 6, 2015, which claims priority to Swedish Patent Application No. 1450263-7, filed Mar. 7, 2014, the disclosures of both of which are incorporated herein by reference in their entireties.

TECHNICAL FIELD

The present invention relates to novel tricyclic compounds comprising a residue of a thiol, pharmaceutical compositions comprising such compounds, and a method of treating or alleviating conditions, in particular cancer, by use of such compounds.

BACKGROUND

Cancer is a heterogeneous disease. Accordingly any treatment should be adopted for given type of cancer as determined by the location and genetic makeup of the tumor. However, although cancer is a heterogeneous disease, all forms of cancer show some fundamental similarities including uncontrolled growth and self-renewal. So despite different genetic backgrounds different cancers have common traits and this is in some ways driven by the pattern of gene expression. Since many different signals, regardless of cause, converge on transcription factors, and since the activation of transcription factors is a nodal point for gene transcription, transcription factors should be convergent targets for treating cancer.

Transcription factors are essential cellular components mediating different extracellular signals, including developmental and environmental, by binding to transcription responsive elements in the genome and thereby initiating the transcription of specific target genes. Aberrant transcription factor function is often associated with different diseases and leads to either increased or excessive gene transcription. As many signals and activating mechanisms converge on single transcription factors they could make efficient drug targets, e.g. for treatment of cancer.

Latent cytoplasmic transcription factors (LCTFs) are transcription factors that reside in the cytoplasm in an inactive form until they are activated through an external signal often in the form of a cell surface receptor-ligand interaction. Among these transcription factors are the family of Signal Transducer and Activator of Transcription (STAT) proteins. The STAT proteins have dual roles as they can act as both transducers of signals through the cytoplasm and function as transcription factors in the nucleus.

STAT3 is one of 6 members of the STAT family of transcriptions factors. It is an approx. 770 amino acid long protein with 6 subunits or domains; N-terminal, coiled-coil, DNA-binding, linker, SH2 and transactivation domains. STAT3 is activated by cytokine, growth factor and non-receptor mediated signaling. The canonical mechanism of STAT3 activation is kinase mediated phosphorylation of tyrosine 705 (Y705) in the SH2 domain. This triggers a reciprocal recognition of two SH2 domains of STAT3 monomers leading to the formation of a STAT3 dimer. This dimer is translocated to the nucleus, aided by importins, and transcription of target genes, through binding to DNA, is activated. On its way to the nucleus STAT3 can be further modified through serine phosphorylation, lysine acetylation or Small Ubiquitin-like Modifier (SUMO) protein attachment and these modifications serve to modulate the transcriptional activity of STAT3

STAT3 activation and dimerization through phosphorylation can be achieved through at least three responses. STAT3 can be phosphorylated by JAK kinases that are constitutively bound to cytokine receptors. Upon ligand binding, the receptors aggregate and the JAK2 proteins undergo reciprocal activation through phosphorylation and they can then recruit and activate STAT3 through binding to the SH2 domain. Alternatively growth factor receptors can directly recruit and associate with STAT3 leading to STAT3 activation through their receptor tyrosine kinase activity. Finally, non-receptor kinases, e.g. Src family kinases and Abl, can also activate STAT3. In addition non-phosphorylated STAT3 can be transported into the nucleus and participate in transcription probably by binding to other proteins to form functional heteromeric transcription factors. In the nucleus STAT3 can interact with several other proteins including other transcription factors e.g. NF-κB.

STAT3 can also be activated by phosphorylation on serine 727 by various kinases. This phosphorylation leads to enhanced transcriptional activity. Constitutively phosphorylated serine 727 is widespread in cells from patients suffering from chronic lymphocytic leukemia (CLL).

Since STAT3 activation under normal conditions is transient, multiple negative feedback systems exist. STAT3 signaling is tightly regulated and it is not constitutively activated in normal tissue. Several endogenous negative regulators for STAT3 signaling have been found and these include Suppressor of cytokine signaling (SOCS, that bind to and inactivate JAKs) and protein inhibitor of activated STAT (PIAS). SOCS is also a gene product of STAT3 transcription demonstrating this as a negative feedback loop. Loss of PIAS or SOCS function or reduced expression will increase STAT3 activation and mutations of these regulatory factors have been found in diseases related to increase STAT3 signaling.

Finally STAT3 is dephosphorylated in the nucleus by different phosphatases and the dephophorylated STAT3 monomers are transported out of the nucleus where they once again reside latent.

The target genes of STAT3 transcription are involved in cell growth and cell cycle regulation (e.g. Cyclin D1, c-Myc, p27), apoptosis (e.g. Mcl-1, survivin, Bcl-2, and Bcl-xL), angiogenesis (VEGF) and metastasis (e.g. MMP-2, MMP-3).

STAT3 can be activated by cytokines and growth factors including IL6, LIF, IL-10, IL-1, IL-12, EGF, TGFalpha, PDGF and G-CSF and various tyrosine and serine kinases including JAK, JAK2, JAK3, TYK2, Src, Src, Lck, Hck, Lyn, Fyn, Fgr, EGFR, ErbB-2, Grb2, JNK, P38MAPK and ERK.

STAT3 is an experimentally validated target in several cancer forms, including leukemia, lymphomas, multiple myeloma, breast cancer, prostate carcinoma, lung cancer (non-small-cell), renal cell carcinoma lung cancer, hepatocellular carcinoma, cholangiocarcinoma, ovarian carcinoma, pancreatic adenocarcinoma, melanoma, head and neck squamous cell carcinoma (Johnston, P. A; Grandis, J. R. Mol Interv. 2011 11(1): 18-26). STAT3 signaling is involved in proliferation, survival, metastasis, drug resistance and migration of cancer cells and it also links inflammation and cancer. This has been demonstrated in numerous studies in vitro, using primary cells or immortalized cell lines, or in vivo using xenograft models (cf. e.g. Sansone, P; Bromberg, J. J Clin Oncol. 2012; 30(9):1005-14, and Miklossy, G.;

Hilliard, T. S.; Turkson, J. Nat Rev Drug Discov. 2013 12(8):611-29) and as such is believed to be an ideal target for cancer therapy (Yu, H.; Lee, H.; Herrmann, A.; Buettner, R.; Jove, R. Nat Rev Cancer. 2014 14(11):736-46.

The sensitivity of many cancer cell lines to STAT3 inhibition indicates an oncogene signaling dependence.

Inflammation and immunity are also important parts of cancer etiology. Cancer cells can promote inflammation in the tumor microenvironment and avoid the innate immune system. STAT3 signaling plays an important dual role in this process. STAT3 is activated by pro-inflammatory cytokine signaling and STAT3 activation opposes T-helper cell anti-tumor responses. Ablation of STAT3 signaling leads to a potent immunological antitumor response. STAT3 is more activated in tumor infiltrating immune cells than in normal tissue and targeting STAT3 causes therapeutic antitumor immunity.

In summary aberrant and deregulated STAT3 promotes cell proliferation and cell survival in both solid and hematological tumors, including breast, lung, brain, colon, prostate, lymphoma and leukemia. Direct inhibitors of STAT3 or inhibitors of STAT3 signaling are thus deemed to be able to mitigate or cure those pathological states.

The treatments for prevention, revocation or reduction of diseases like e.g. cancer are in many ways insufficient. Hence, compounds effective in modulating or inhibiting the above described STAT signaling would be desired.

The direct inhibition of STAT3 can be achieved by inhibiting the protein-protein interaction involved in STAT3 dimerization (STAT3 is a dimer of two proteins) or by blocking the protein-DNA interaction required for STAT3 binding to DNA for the initiation of transcription. Alternatively the production (biosynthesis) of STAT3 can be blocked.

The alternative to direct STAT3 inhibition is to inhibit upstream molecules in the signaling cascade responsible for STAT3 activation (e.g. the JAK kinases). The drawback with this approach is that there are multiple ways to activate STAT3.

The STAT3 SH2 has been targeted with peptidomimetics and non-peptide small molecules (e.g. S3I-M2001) to block STAT3-STAT3 dimerization and DNA binding has been blocked with oligodeoxynucleotide decoys while the production of STAT3 has been inhibited by antisense.

(−)-Galiellalactone is a natural product isolated from wood-inhabiting fungi with submicromolar inhibition of IL-6/STAT3 signaling.

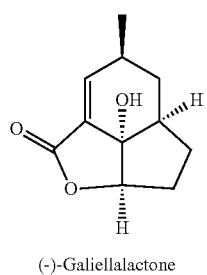

(-)-Galiellalactone

In U.S. Pat. No. 6,512,007 use of galiella lactone as a pharmaceutical for the treatment of e.g. inflammatory processes is disclosed.

The biological effect of (−)-galiellalactone seemingly is due to a direct inhibition of the binding of STAT3-dimers to their regulatory elements (Weidler et al in FEBS Letters 2000, 484, 1-6). Based on this proposed mechanism of action, galiellalactone has been evaluated as an anti-cancer agent. Hellsten et al reported in *Prostate* 68:269-280 (2008) that galiellalactone inhibits the proliferation of STAT3 expressing DU145 prostate cancer cells. Further, Hellsten et al ("*Targeting STAT3 in prostate cancer: Identification of STAT3 as a direct target of the fungal metabolite galiellalactone*" Nicholas Don-Doncow, Zilma Escobar, Martin Johansson, Eduardo Muñoz, Olov Sterner, Anders Bjartell, Rebecka Hellsten. AACR-NCI-EORTC International Conference on Molecular Targets and Cancer Therapeutics, Oct. 19-23, 2013, Boston, Mass. Abstract nr C229; Don-Doncow, N.; Escobar, Z.; Johansson, M.; Kjellström, S.; Garcia, V.; Munoz, E.; Sterner, O.; Bjartell, A.; Hellsten, R. J Biol Chem. 2014 289(23):15969-78) have shown that galiellalactone binds directly and covalently to STAT3, thus inhibiting the transcriptional activity. Galiellalactone is thus a candidate drug for treatment of cancer.

However, galiellalactone has been found to display limited plasma exposure upon oral administration and as such is deemed to not represent a suitable drug for oral delivery. Hence, ways of improving the oral bioavailability and/or other druglike properties of galiellalactone are warranted.

Attempts to modify the activity and properties of galiellalactone have been reported in the art. Nussbaum et al reported in Eur. J. Org. Chem. 2004, 2783-2790 on the modification of individual functional groups of (−)-galiellalactone. Most of the resulting analogues, however, turned out to be completely inactive or much less active than (−)-galiellalactone. Especially, modifications of the conjugated double bond were reported to produce inactive compounds. In PCT/EP2011/062243 preparation and use of novel tricylic compounds, based on a galiellalactone scaffold, that inhibit STAT3 and NF-kB signaling are disclosed.

However none of these modified deratives has been reported to overcome the shortcoming of galiellalactone when administered orally. Thus, there is a need in the art for inhibitors STAT3 having improved drug like properties to achieve sufficient exposure and dosing regimes.

SUMMARY

The present invention seeks to mitigate, alleviate, circumvent or eliminate at least one, such as one or more, of the above-identified deficiencies by providing a compound, according to an aspect, a compound according to formula (I)

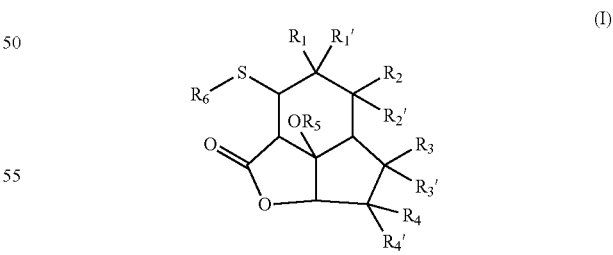

(I)

wherein $R_1$ and $R_1'$ are independently selected from the group consisting of H, C1-5 alkyl, C1-5 fluoroalkyl, halo, C3-8 non-aromatic carbocycle, C0-5 alkyleneOC0-5 alkyl, C0-3 alkyleneOC1-5 fluoroalkyl, C0-3 alkyleneOC(O)C1-5 alkyl, OC2-3 alkyleneN(C0-5 alkyl)$_2$ in which the C0-5 alkyl may be the same or different, C0-3 alkyleneNHC0-5 alkyl, C0-3 alkyleneN(C1-5 alkyl)$_2$ in which the C1-5 alkyl may be the same or different, C0-3 alkyleneN(C0-5 alkyl)C(O)C1-5 alkyl, C0-3 alkyleneNHaryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C0-3 alkyleneNHheteroaryl, wherein said heteroaryl is a 5- or 6-membered heteroaryl, said heteroaryl being unsubstituted or substituted with a one or several independently selected C1-5 alkyl groups, C0-3 alkyleneC(O)NHC0-5 alkyl, C0-3 alkyleneC(O)N(C1-5 alkyl)$_2$ in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C0-3 alkylene heteroaryl, wherein said heteroaryl is a 5- or 6-membered heteroaryl, said heteroaryl being unsubstituted or substituted with a one or several independently selected C1-5 alkyl groups, halo, C0-1 alkylene cyano, SC0-5 alkyl, C0-3 alkyleneSO$_2$C0-5 alkyl, nitro, C(O)C0-C5 alkyl, C(O)C1-C5 fluoroalkyl, N(C0-C3 alkyl)SO$_2$C1-C5 alkyl, and N(C0-C5 alkyl)SO$_2$C1-5 fluoroalkyl;

R$_2$ and R$_2$' are independently selected from the group consisting of H, C1-5 alkyl, C1-5 fluoroalkyl, halo, C3-8 non-aromatic carbocycle, C0-5 alkyleneOC0-5 alkyl, C0-3 alkyleneOC1-5 fluoroalkyl, C0-3 alkyleneOC(O)C1-5 alkyl, OC2-3 alkyleneN(C0-5 alkyl)$_2$ in which the C0-5 alkyl may be the same or different, C0-3 alkyleneNHC0-5 alkyl, C0-3 alkyleneN(C1-5 alkyl)$_2$ in which the C1-5 alkyl may be the same or different, C0-3 alkyleneN(C0-5 alkyl)C(O)C1-5 alkyl, C0-3 alkyleneNHaryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C0-3 alkyleneNHheteroaryl, wherein said heteroaryl is a 5- or 6-membered heteroaryl, said heteroaryl being unsubstituted or substituted with a one or several independently selected C1-5 alkyl groups, C0-3 alkyleneC(O)NHC0-5 alkyl, C0-3 alkyleneC(O)N(C1-5 alkyl)$_2$ in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C0-3 alkylene heteroaryl, wherein said heteroaryl is a 5- or 6-membered heteroaryl, said heteroaryl being unsubstituted or substituted with a one or several independently selected C1-5 alkyl groups, halo, C0-1 alkylene cyano, SC0-5 alkyl, C0-3 alkyleneSO$_2$C0-5 alkyl, nitro, C(O)C0-C5 alkyl, C(O)C1-C5 fluoroalkyl, N(C0-C3 alkyl)SO$_2$C1-C5 alkyl, and N(C0-C5 alkyl)SO$_2$C1-5 fluoroalkyl;

R$_3$ and R$_3$' are independently selected from the group consisting of H, C1-5 alkyl, C1-5 fluoroalkyl, halo, C3-8 non-aromatic carbocycle, C0-5 alkyleneOC0-5 alkyl, C0-3 alkyleneOC1-5 fluoroalkyl, C0-3 alkyleneOC(O)C1-5 alkyl, OC2-3 alkyleneN(C0-5 alkyl)$_2$ in which the C0-5 alkyl may be the same or different, C0-3 alkyleneNHC0-5 alkyl, C0-3 alkyleneN(C1-5 alkyl)$_2$ in which the C1-5 alkyl may be the same or different, C0-3 alkyleneN(C0-5 alkyl)C(O)C1-5 alkyl, C0-3 alkyleneNHaryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C0-3 alkyleneNHheteroaryl, wherein said heteroaryl is a 5- or 6-membered heteroaryl, said heteroaryl being unsubstituted or substituted with a one or several independently selected C1-5 alkyl groups, C0-3 alkyleneC(O)NHC0-5 alkyl, C0-3 alkyleneC(O)N(C1-5 alkyl)$_2$ in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C0-3 alkylene heteroaryl, wherein said heteroaryl is a 5- or 6-membered heteroaryl, said heteroaryl being unsubstituted or substituted with a one or several independently selected C1-5 alkyl groups, halo, C0-1 alkylene cyano, SC0-5 alkyl, C0-3 alkyleneSO$_2$C0-5 alkyl, nitro, C(O)C0-C5 alkyl, C(O)C1-C5 fluoroalkyl, N(C0-C3 alkyl)SO$_2$C1-C5 alkyl, and N(C0-C5 alkyl)SO$_2$C1-5 fluoroalkyl;

R$_4$ and R$_4$' are independently selected from the group consisting of H, C1-5 alkyl, C1-5 fluoroalkyl, halo, C3-8 non-aromatic carbocycle, C0-5 alkyleneOC0-5 alkyl, C0-3 alkyleneOC1-5 fluoroalkyl, C0-3 alkyleneOC(O)C1-5 alkyl, OC2-3 alkyleneN(C0-5 alkyl)$_2$ in which the C0-5 alkyl may be the same or different, C0-3 alkyleneNHC0-5 alkyl, C0-3 alkyleneN(C1-5 alkyl)$_2$ in which the C1-5 alkyl may be the same or different, C0-3 alkyleneN(C0-5 alkyl)C(O)C1-5 alkyl, C0-3 alkyleneNHaryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C0-3 alkyleneNHheteroaryl, wherein said heteroaryl is a 5- or 6-membered heteroaryl, said heteroaryl being unsubstituted or substituted with a one or several independently selected C1-5 alkyl groups, C0-3 alkyleneC(O)NHC0-5 alkyl, C0-3 alkyleneC(O)N(C1-5 alkyl)$_2$ in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C0-3 alkylene heteroaryl, wherein said heteroaryl is a 5- or 6-membered heteroaryl, said heteroaryl being unsubstituted or substituted with a one or several independently selected C1-5 alkyl groups, halo, C0-1 alkylene cyano, SC0-5 alkyl, C0-3 alkyleneSO$_2$C0-5 alkyl, nitro, C(O)C0-C5 alkyl, C(O)C1-C5 fluoroalkyl, N(C0-C3 alkyl)SO$_2$C1-C5 alkyl, and N(C0-C5 alkyl)SO$_2$C1-5 fluoroalkyl;

R$_5$ is selected from the group consisting of H, C1-5 alkyl, C1-5 fluoroalkyl, C(O)C1-5 alkyl, C2-3 alkyleneN(C0-5 alkyl)$_2$ in which the C0-5 alkyl may be the same or different, C(O)N(0-5 alkyl)$_2$ in which the C0-5 alkyl may be the same or different, C(O)aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C(O)heteroaryl, wherein said heteroaryl is a 5- or 6-membered heteroaryl, said heteroaryl being unsubstituted or substituted with a one or several independently selected C1-5 alkyl groups, C(O)C1-C3alkylenearyl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, and C(O)C1-C3alkyleneheteroaryl, wherein said heteroaryl is a 5- or 6-membered heteroaryl, said heteroaryl being unsubstituted or substituted with a one or several independently selected C1-5 alkyl groups; and $R_6$ is selected from the group consisting of H, C1-8 alkyl, C1-8 fluoroalkyl, C3-C8 alkyleneN(C1-5 alkyl)$_2$ in which the C1-5 alkyl may be the same or different, C2-5 alkyleneOC0-5 alkyl, C2-3 alkyleneOC1-5 fluoroalkyl, C2-3 alkyleneOC(O)C1-5 alkyl, C3-5 alkyleneNHC0-5 alkyl, C2-3 alkyleneN(C0-5 alkyl)C(O)C1-5 alkyl, C2-5 alkyleneN-Haryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano, and N(C0-5 alkyl)$_2$ in which the C0-5 alkyl may be the same or different, C2-5 alkyleneNHheteroaryl, wherein said heteroaryl is a 5- or 6-membered heteroaryl, said heteroaryl being unsubstituted or substituted with a one or several independently selected C1-5 alkyl groups, C1-3 alkyleneC(O)NHC0-5 alkyl, C1-3 alkyleneC(O)N(C1-5 alkyl)$_2$ in which the C1-5 alkyl may be the same or different, C1-3 alkyleneC(O)N(C4-5 alkylene), C1-3 alkyleneC(O)OC0-5 alkyl, a 3- to 8-membered non-aromatic heterocycle, C2-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C1-3 alkylene heteroaryl, wherein said heteroaryl is a 5- or 6-membered heteroaryl, said heteroaryl being unsubstituted or substituted with a one or several independently selected C1-5 alkyl groups, C1-3 alkyleneSO$_2$C0-5 alkyl, C1-5 alkyleneSO$_3$H, aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, heteroaryl, wherein said heteroaryl is a 5- or 6-membered heteroaryl, said heteroaryl being unsubstituted or substituted with a one or several independently selected C1-5 alkyl groups, and moieties according to formula (II),

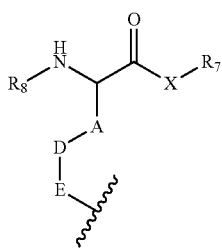

(II)

wherein the waved line indicates the point of attachment to the sulfur atom in formula (I);

A is a C1-5 alkylene;
D is a bond a phenylene, or a heteroarylene, wherein said heteroarylene is a 5- or 6-membered heteroarylene;
E is a bond or a C1-5 alkylene;
X is NC0-C5 alkyl or "O" (oxygen);
$R_7$ is selected from the group consisting of H, provided that X is NC0-C5 alkyl, $R_7$ is not to be H if X is "O" (oxygen), C1-C10 alkyl, C1-5 alkyleneN(C1-5 alkyl)$_2$ in which the C1-5 alkyl may be the same or different, C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C1-3 alkylene heteroaryl, wherein said heteroaryl is a 5- or 6-membered heteroaryl, said heteroaryl being unsubstituted or substituted with a one or several independently selected C1-5 alkyl groups, an amino acid residue selected from the group consisting alanine, arginine, asparagine, aspartic acid, cysteine, glutamine, glutamic acid, glycine, histidine, isoleucine, leucine, lysine; methionine, phenylalanine, proline, threonine, tryptophan, tyrosine and valine, which amino acid residue is connected to the moiety according to formula (II) at the N-terminal of the amino acid residue and optionally esterfied at the C-terminal with a C1-5 monohydric alkanol, and a di-, a tri-, or a tetrapeptide residue, wherein the amino acid residues in said peptide residue are independently selected from the group consisting alanine, arginine, asparagine, aspartic acid, cysteine, glutamine, glutamic acid, glycine, histidine, isoleucine, leucine, lysine; methionine, phenylalanine, proline, threonine, tryptophan, tyrosine and valine, the peptide residue being connected to the moiety according to formula (II) at the N-terminal of the peptide and optionally esterfied at the C-terminal with a C1-5 monohydric alkanol; and $R_8$ is selected from the group consisting of C(O)C1-C6 alkyl, C(O)OC1-C6 alkyl, C(O)C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C(O)C0-3 alkylene heteroaryl, wherein said heteroaryl is a 5- or 6-membered heteroaryl, said heteroaryl being unsubstituted or substituted with a one or several independently selected C1-5 alkyl groups, an amino acid residue selected from the group consisting alanine, arginine, asparagine, aspartic acid, cysteine, glutamine, glutamic acid, glycine, histidine, isoleucine, leucine, lysine; methionine, phenylalanine, proline, threonine, tryptophan, tyrosine and valine, which amino acid residue is connected to the moiety according to formula (II) at the C-terminal of the amino acid residue, and which amino acid residue optionally is N-acylated, wherein said acyl group is selected from the group consisting C(O)C1-C6 alkyl, and C(O)C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, and a di-, a tri-, or a tetrapeptide residue, wherein the amino acid residues in said peptide residue are independently selected from the group consisting alanine, arginine, asparagine, aspartic acid, cysteine, glutamine, glutamic acid, glycine, histidine, isoleucine, leucine, lysine; methionine, phenylalanine, proline, threonine, tryptophan, tyrosine and valine, the peptide residue being connected to the moiety according to formula (II) at the C-terminal of the peptide, and the N-terminal of the peptide optionally being N-acelyated, wherein said acyl group is selected from the group consisting C(O)C1-C6 alkyl and C(O)C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different;

as a free base, an acid in its non-charged protonated form, a pharmaceutically acceptable addition salt, solvate, solvate of a salt thereof, a pure diastereomer, a pure enantiomer, a diastereomeric mixture, a racemic mixture, a scalemic mixture, a corresponding tautomeric form resulting from a hydrogen shift between two hetero-atoms and/or the corresponding tautomeric form resulting from a keto-enol tautomerization.

According to another aspect, there is provided a pharmaceutical composition comprising a compound according to formula (I) and at least one pharmaceutically acceptable carrier or excipient. Such compound and composition are useful in therapy.

According to another aspect, compounds according to formula (I) and compositions comprising such compounds are useful in the treatment of STAT3 signaling related disorders as well as in treatment of diseases and disorders selected from the group consisting of: solid cancers, hematological cancers, benign tumors, hyperproliferative diseases, inflammations, autoimmune diseases, graft or transplant rejections, delayed physiological function of grafts or transplants, neurodegenerative diseases and viral infections, such as from solid cancers and hematological cancers.

Further, advantageous features of various embodiments of the invention are defined in the dependent claims and within the detailed description below.

DETAILED DESCRIPTION

Definitions

In the context of the present application and invention, the following definitions apply:

The term "addition salt" is intended to mean salts formed by the addition of a pharmaceutical acceptable acid, such as organic or inorganic acids, or a pharmaceutical acceptable base. The organic acid may be, but is not limited to, acetic, propanoic, methanesulfonic, benzenesulfonic, lactic, malic, citric, tartaric, succinic or maleic acid. The inorganic acid may be, but is not limited to, hydrochloric, hydrobromic, sulfuric, nitric acid or phosphoric acid. The base may be, but is not limited to, ammonia and hydroxides of alkali or alkaline earth metals. The term "addition salt" also comprises the hydrates and solvent addition forms, such as hydrates and alcoholates.

As used herein, "halo" or "halogen" refers to fluoro, chloro, bromo, and iodo.

As used herein, "alkyl" used alone or as a suffix or prefix, is intended to include both branched and straight chain saturated aliphatic hydrocarbon groups having from 1 to 12 carbon atoms or if a specified number of carbon atoms is provided then that specific number is intended. For example "C1-6 alkyl" denotes alkyl having 1, 2, 3, 4, 5 or 6 carbon atoms. When the specific number denoting the alkyl group is the integer 0 (zero), no alkyl group having from 1 to 12 carbon atoms is present and a hydrogen atom is instead present as the substituent. For example, "N(C0 alkyl)$_2$" is equivalent to "NH$_2$" (amino), C0 alkyl is equivalent to H (hydrogen), and OC0 alkyl is equivalent to OH (hydroxy).

Examples of alkyl include, but are not limited to, methyl, ethyl, n-propyl, i-propyl, n-butyl, i-butyl, sec-butyl, t-butyl, pentyl, and hexyl.

As used herein, "alkylenyl" or "alkylene" used alone or as a suffix or prefix, is intended to include straight chain saturated aliphatic hydrocarbon groups having from 1 to 12 carbon atoms or if a specified number of carbon atoms is provided then that specific number is intended. For example "C1-6 alkylenyl" or "C1-6 alkylene" denotes alkylenyl or alkylene having 1, 2, 3, 4, 5 or 6 carbon atoms. When the specific number denoting the alkylenyl or alkylene group is the integer 0 (zero), no alkylenyl or alkylene group having from 1 to 12 carbon atoms is present and instead a bond directly links the groups specified at each end of the alkylenyl or alkylene group. For example, "NH(C0 alkylene)NH$_2$" is equivalent to "NHNH$_2$" (hydrazino). As used herein, the groups linked by an alkylene or alkylenyl group are intended to be attached to the first and to the last carbon of the alkylene or alkylenyl-group. As explained immediately above, when the alkylenyl or alkylene group is C0 alkylenyl or C0 alkylene, the group represents a bond and the linked groups are thus directly linked to each other. In the case of methylene, the first and the last carbon is the same. For example, "H$_2$N(C2 alkylene)NH$_2$", "H$_2$N(C3 alkylene) NH$_2$", "N(C4 alkylene)", "N(C5 alkylene)" and "N(C2 alkylene)$_2$NH" is equivalent to 1,2-diamino ethane, 1,3-diamino propane, pyrrolidinyl, piperidinyl and piperazinyl, respectively. Examples of alkylene or alkylenyl include, but are not limited to, methylene, ethylene, propylene, and butylene.

As used herein, "alkoxy" or "alkyloxy" is intended to mean an alkyl group as defined above with the indicated number of carbon atoms attached through an oxygen bridge. Examples of alkoxy include, but are not limited to, methoxy, ethoxy, n-propoxy, isopropoxy, n-butoxy, isobutoxy, t-butoxy, n-pentoxy, isopentoxy, cyclopropylmethoxy, allyloxy and propargyloxy. Similarly, "alkylthio" or "thioalkoxy" represent an alkyl group as defined above with the indicated number of carbon atoms attached through a sulphur bridge.

As used herein, "fluoroalkyl", "fluoroalkylene" and "fluoroalkoxy", used alone or as a suffix or prefix, refers to groups in which one, two, or three of the hydrogen(s) attached to any of the carbons of the corresponding alkyl, alkylene and alkoxy-groups are replaced by fluoro.

Examples of fluoroalkyl include, but are not limited to, trifluoromethyl, difluoromethyl, fluoromethyl, 2,2,2-trifluoroethyl, 2-fluoroethyl and 3-fluoropropyl.

Examples of fluoroalkylene include, but are not limited to, difluoromethylene, fluoromethylene, 2,2-difluorobutylene and 2,2,3-trifluorobutylene.

Examples of fluoroalkoxy include, but are not limited to, trifluoromethoxy, 2,2,2-trifluoroethoxy, 3,3,3-trifluoropropoxy and 2,2-difluoropropoxy.

As used herein, "non-aromatic carbocycle", whether alone or as a suffix or prefix, is intended to mean non-aromatic saturated and unsaturated carbomonocycles, having from 3 to 8 ring carbon atoms, such as cyclopropanyl, cyclopentanyl, cyclohexanyl, cyclopentenyl and cyclohexenyl. If a prefix, such as C3-C6, is given, when said carbocycle comprises the indicated number of carbon atoms, eg. 3, 4, 5 or 6 carbon atoms. Accordingly, "C6 non-aromatic carbocycle" for example includes cyclohexyl and cyclohexenyl. Non-aromatic unsaturated carbocycles are to be distinguished from aryls, as aryl refers to aromatic ring structures, comprising at least one aromatic ring.

As used herein, "cycloalkyl", whether alone or as a suffix or prefix, is intended to mean a saturated carbomonocycle, having from 3 to 8 ring carbon atoms, such as cyclopropanyl, cyclopentanyl and cyclohexanyl. If a prefix, such as C3-C6, is given, when said cycloalkyl comprises the indicated number of carbon atoms, e.g. 3, 4, 5 or 6 carbon atoms. Accordingly, C6 cycloalkyl corresponds to cyclohexyl.

As used herein, "cycloalkenyl", whether alone or as a suffix or prefix, is intended to mean a monounsaturated carbomonocycle, having from 4 to 8 ring carbon atoms, such as cyclopentenyl and cyclohexenyl. If a prefix, such as C3-C6, is given, when said cycloalkenyl comprises the indicated number of carbon atoms, eg. 3, 4, 5 or 6 carbon atoms. Accordingly, C6 cycloalkenyl corresponds to cyclohexenyl.

As used herein, the term "substitutable" refers to an atom to which hydrogen may be covalently attached, and to which another substituent may be present instead of the hydrogen. A non-limiting example of substitutable atoms includes the carbon-atoms of pyridine. The nitrogen-atom of pyridine is not substitutable according to this definition. Further, according to the same definition, the imine nitrogen at position 3 in imidazole is not substitutable, while the amine nitrogen at position 1 is.

As used herein, the term "aryl" refers to a ring structure, comprising at least one aromatic ring, made up of from 5 to 14 carbon atoms. Ring structures containing 5, 6, or 7 carbon atoms would be single-ring aromatic groups, for example phenyl. Ring structures containing 8, 9, 10, 11, 12, 13, or 14 carbon atoms would be polycyclic, for example naphthyl. The aromatic ring may be substituted at one or more ring positions. The term "aryl" also includes polycyclic ring systems having two or more cyclic rings in which two or more carbons are common to two adjoining rings (the rings are "fused rings") wherein at least one of the rings is aromatic, for example, the other cyclic rings may be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

As used herein, "heteroaryl" or "hetaryl" refers to an aromatic heterocycle, having at least one ring with aromatic character, (e.g. 6 delocalized electrons) or at least two conjugated rings with aromatic character, (e.g. 4n+2 delocalized electrons where "n" is an integer), and comprising up to about 14 carbon atoms, and having at least one heteroatom ring member such as sulfur, oxygen, or nitrogen. Heteroaryl or hetaryl groups include monocyclic and bicyclic (e.g., having 2 fused rings) systems. The aromatic ring of the heteroaryl or hetaryl group may be substituted at one or more ring positions.

Examples of heteroaryl or hetaryl groups include without limitation, pyridyl (i.e., pyridinyl), pyrimidinyl, pyrazinyl, pyridazinyl, triazinyl, furyl (i.e. furanyl), quinolyl, tetrahydroquinolyl, isoquinolyl, tetrahydroisoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, benzimidazolyl, indolinyl, and the like.

As used herein, "non-aromatic heterocycle" refers to a monocycle comprising at least one heteroatom ring member, such as sulfur, oxygen, or nitrogen. Such monocyclic rings may be saturated or unsaturated. However, non-aromatic heterocycles are to be distinguished from heteroaryl groups.

Examples of non-aromatic heterocycle groups include without limitation morpholinyl, piperazinyl, 3H-diazirin-3-yl, oxiranyl, aziridinyl, piperidinyl, pyrrolidinyl, tetrahydrofuranyl, tetrahydropyranyl, dihydro-2H-pyranyl.

As used herein, the term "relative stereochemistry", such as when e.g. referring to e.g. a drawing of a structure, is relating to the relative spatial arrangement of e.g. substituents or groups of a structure. For example, if the relative stereochemistry is indicated by drawing substituents or groups of a molecule in certain directions, the corresponding mirror image of that molecule will have the same relative stereochemistry. On the other hand, if the "absolute stereochemistry" is indicated by drawing substituents or groups of a molecule in certain directions, a particular enantiomer of that molecule is intended.

EMBODIMENTS OF THE INVENTION

Previously, galiellactone has only been administered intraperitoneally (ip) for in vivo studies. When the oral administration of galiellalactone (10 mg/kg) was investigated in mice, only very low plasma levels of galiellalactone were achieved ($C_{max}$=52 ng/ml and $AUC_{0-\infty}$=5.7 µg/mL·min). The data suggested that this was due to poor absorption.

One way of increasing the bioavailability of a compound with low plasma exposure is to make a prodrug of the active parent drug. The prodrug can e.g. increase the absorption after oral administration. After uptake the prodrug should preferably be converted to the active parent compound either through metabolism or spontaneous chemical reactions. One measure of improved drug like properties is the plasma exposure of the active parent compound as measured over time (AUC).

Galiellalactone is a reactive Michael acceptor. From the literature it is known that reactive Michael acceptors can be converted to prodrugs with improved drug like properties by reacting them with different amines to give amine-adducts (Woods et al *Med. Chem. Commun.*, 2013, 4, 27-33). This has for example been done with parthenolide (Neelakantan et al Bioorganic & Medicinal Chemistry Letters 19 (2009) 4346-4349) and arglabin. The amine-drug adducts are then converted in vivo to the active parent compound.

Galiellalactone was therefore reacted with pyrrolidine to make an amine-galiellalactone adduct that could act as a potential prodrug. However, when dosed orally (10 mg/kg) in mice the plasma levels of galiellalactone were not improved at all compared to when galiellalactone was dosed orally (cf. experimental parts below for details).

The chemical stability of the pyrrolidine-galiellalactone adduct was investigated in 0.1 M PBS (pH 7.4) and it was found that it was very unstable and it was found to be rapidly converted to galiellactone. It was envisaged that the lack of improved plasma exposure of the prodrug might be due to its chemical instability. A series of amine-galiellalactone adducts were evaluated for their chemical stability, but all were found to be unstable in 0.1 M PBS (pH 7.4).

Also thiols, such as cysteine, may be used to convert Michael acceptors to prodrugs. The addition of cysteine and cysteine Me-ester adducts of galiellalactone was confirmed to be reversible, thus also such adducts represents potential pro-drug candidates. However, similarly to the amine adducts, the cysteine and cysteine Me-ester adducts of galiellalactone were unstable in 0.1 M PBS (pH 7.4), thus precluding their use as prodrugs.

In order to provide a prodrug of galiellalactone, improving the bioavailability subsequent to oral administration, it was deemed necessary to provide chemically more stable adducts.

It was surprisingly found that the general low stability seen for amine adducts of galiellalactone is not seen among thiols adducts in general. Especially, it was found that use of N-acelyated cysteine Me-ester provided a thiol adduct of galiellalactone being chemically stable in 0.1 M PBS (pH 7.4; cf. experimental parts below for details).

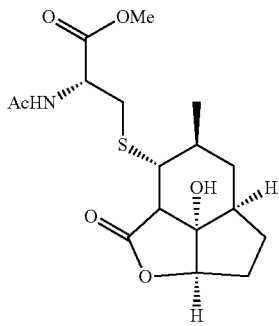

N-acelyated cysteine Me-ester adduct of galiellalactone

Upon evaluation in vivo, the adduct was found to significantly improve the plasma exposures of galiellalactone, compared to oral administration of galiellalactone itself.

Further, it was found that also other thiol adducts had similar properties. Without being bound to any theory, it seems that the amino group of the cysteine adduct provides means for intramolecularly assisting a retro Michael attack releasing the Michael acceptor, i.e. galiellactone. Acylation, amidation, removal of the amino group (beta to the sulfur atom of the cystein residue) all resulted in adducts with improved stability and improved plasma exposures of galiellalactone compared to oral administration of galiellalactone itself. Further, amino groups in other positions than beta to the sulfur atom of the cystein residue did seemingly not result in adducts being unstable in PBS. As an example, reacting the methyl ester of the di-peptide Val-Cys with galiellactone resulted in a compound (cf. formula below) being chemically stable in 0.1 M PBS.

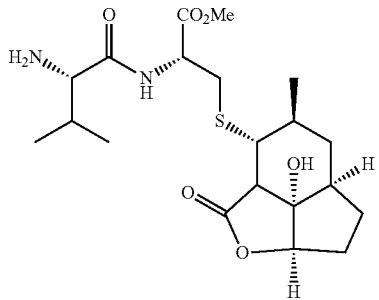

Thus, an embodiment relates to a compound according to formula (I)

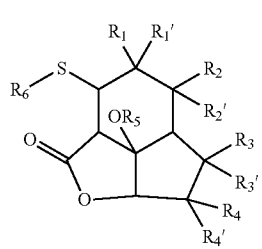

(I)

wherein $R_1$ and $R_1'$ are independently selected from the group consisting of H, C1-5 alkyl, C1-5 fluoroalkyl, halo, C3-8 non-aromatic carbocycle, C0-5 alkyleneOC0-5 alkyl, C0-3 alkyleneOC1-5 fluoroalkyl, C0-3 alkyleneOC(O)C1-5 alkyl, OC2-3 alkyleneN(C0-5 alkyl)$_2$ in which the C0-5 alkyl may be the same or different, C0-3 alkyleneNHC0-5 alkyl, C0-3 alkyleneN(C1-5 alkyl)$_2$ in which the C1-5 alkyl may be the same or different, C0-3 alkyleneN(C0-5 alkyl)C(O)C1-5 alkyl, C0-3 alkyleneNHaryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C0-3 alkyleneNHheteroaryl, wherein said heteroaryl is a 5- or 6-membered heteroaryl, said heteroaryl being unsubstituted or substituted with a one or several independently selected C1-5 alkyl groups, C0-3 alkyleneC(O)NHC0-5 alkyl, C0-3 alkyleneC(O)N(C1-5 alkyl)$_2$ in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C0-3 alkylene heteroaryl, wherein said heteroaryl is a 5- or 6-membered heteroaryl, said heteroaryl being unsubstituted or substituted with a one or several independently selected C1-5 alkyl groups, halo, C0-1 alkylene cyano, SC0-5 alkyl, C0-3 alkyleneSO$_2$C0-5 alkyl, nitro, C(O)C0-C5 alkyl, C(O)C1-C5 fluoroalkyl, N(C0-C3 alkyl)SO$_2$C1-C5 alkyl, and N(C0-C5 alkyl)SO$_2$C1-5 fluoroalkyl;

$R_2$ and $R_2'$ are independently selected from the group consisting of H, C1-5 alkyl, C1-5 fluoroalkyl, halo, C3-8 non-aromatic carbocycle, C0-5 alkyleneOC0-5 alkyl, C0-3 alkyleneOC1-5 fluoroalkyl, C0-3 alkyleneOC(O)C1-5 alkyl, OC2-3 alkyleneN(C0-5 alkyl)$_2$ in which the C0-5 alkyl may be the same or different, C0-3 alkyleneNHC0-5 alkyl, C0-3 alkyleneN(C1-5 alkyl)$_2$ in which the C1-5 alkyl may be the same or different, C0-3 alkyleneN(C0-5 alkyl)C(O)C1-5 alkyl, C0-3 alkyleneNHaryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C0-3 alkyleneNHheteroaryl, wherein said heteroaryl is a 5- or 6-membered heteroaryl, said heteroaryl being unsubstituted or substituted with a one or several independently selected C1-5 alkyl groups, C0-3 alkyleneC(O)NHC0-5 alkyl, C0-3 alkyleneC(O)N(C1-5 alkyl)$_2$ in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C0-3 alkylene heteroaryl, wherein said heteroaryl is a 5- or 6-membered heteroaryl, said heteroaryl being unsubstituted or substituted with a one or several independently selected C1-5 alkyl groups, halo, C0-1 alkylene cyano, SC0-5 alkyl, C0-3 alkyleneSO$_2$C0-5 alkyl, nitro, C(O)C0-C5 alkyl, C(O)C1-C5 fluoroalkyl, N(C0-C3 alkyl)SO$_2$C1-C5 alkyl, and N(C0-C5 alkyl)SO$_2$C1-5 fluoroalkyl;

$R_3$ and $R_3'$ are independently selected from the group consisting of H, C1-5 alkyl, C1-5 fluoroalkyl, halo, C3-8 non-aromatic carbocycle, C0-5 alkyleneOC0-5 alkyl, C0-3 alkyleneOC1-5 fluoroalkyl, C0-3 alkyleneOC(O)C1-5 alkyl, OC2-3 alkyleneN(C0-5 alkyl)$_2$ in which the C0-5 alkyl may be the same or different, C0-3 alkyleneNHC0-5 alkyl, C0-3 alkyleneN(C1-5 alkyl)$_2$ in which the C1-5 alkyl may be the same or different, C0-3 alkyleneN(C0-5 alkyl)C(O)C1-5 alkyl, C0-3 alkyleneNHaryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C0-3 alkyleneNHheteroaryl, wherein said heteroaryl is a 5- or 6-membered heteroaryl, said heteroaryl being unsubstituted or substituted with a one or several independently selected C1-5 alkyl groups, C0-3 alkyleneC(O)NHC0-5 alkyl, C0-3 alkyleneC(O)N(C1-5 alkyl)$_2$ in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C0-3 alkylene heteroaryl, wherein said heteroaryl is a 5- or 6-membered heteroaryl, said heteroaryl being unsubstituted or substituted with a one or several independently selected C1-5 alkyl groups, halo, C0-1 alkylene cyano, SC0-5 alkyl, C0-3 alkyleneSO$_2$C0-5 alkyl, nitro, C(O)C0-C5 alkyl, C(O)C1-C5 fluoroalkyl, N(C0-C3 alkyl)SO$_2$C1-C5 alkyl, and N(C0-C5 alkyl)SO$_2$C1-5 fluoroalkyl;

$R_4$ and $R_4'$ are independently selected from the group consisting of H, C1-5 alkyl, C1-5 fluoroalkyl, halo, C3-8 non-aromatic carbocycle, C0-5 alkyleneOC0-5 alkyl, C0-3 alkyleneOC1-5 fluoroalkyl, C0-3 alkyleneOC(O)C1-5 alkyl, OC2-3 alkyleneN(C0-5 alkyl)$_2$ in which the C0-5 alkyl may be the same or different, C0-3 alkyleneNHC0-5 alkyl, C0-3 alkyleneN(C1-5 alkyl)$_2$ in which the C1-5 alkyl may be the same or different, C0-3 alkyleneN(C0-5 alkyl)C(O)C1-5 alkyl, C0-3 alkyleneNHaryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C0-3 alkyleneNHheteroaryl, wherein said heteroaryl is a 5- or 6-membered heteroaryl, said heteroaryl being unsubstituted or substituted with a one or several independently selected C1-5 alkyl groups, C0-3 alkyleneC(O)NHC0-5 alkyl, C0-3 alkyleneC(O)N(C1-5 alkyl)$_2$ in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C0-3 alkylene heteroaryl, wherein said heteroaryl is a 5- or 6-membered heteroaryl, said heteroaryl being unsubstituted or substituted with a one or several independently selected C1-5 alkyl groups, halo, C0-1 alkylene cyano, SC0-5 alkyl, C0-3 alkyleneSO$_2$C0-5 alkyl, nitro, C(O)C0-C5 alkyl, C(O)C1-C5 fluoroalkyl, N(C0-C3 alkyl)SO$_2$C1-C5 alkyl, and N(C0-C5 alkyl)SO$_2$C1-5 fluoroalkyl;

$R_5$ is selected from the group consisting of H, C1-5 alkyl, C1-5 fluoroalkyl, C(O)C1-5 alkyl, C2-3 alkyleneN(C0-5 alkyl)$_2$ in which the C0-5 alkyl may be the same or different, C(O)N(0-5 alkyl)$_2$ in which the C0-5 alkyl may be the same or different, C(O)aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C(O)heteroaryl, wherein said heteroaryl is a 5- or 6-membered heteroaryl, said heteroaryl being unsubstituted or substituted with a one or several independently selected C1-5 alkyl groups, C(O)C1-C3alkylenearyl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, and C(O)C1-C3alkyleneheteroaryl, wherein said heteroaryl is a 5- or 6-membered heteroaryl, said heteroaryl being unsubstituted or substituted with a one or several independently selected C1-5 alkyl groups; and $R_6$ is selected from the group consisting of H, C1-8 alkyl, C1-8 fluoroalkyl, C3-C8 alkyleneN(C1-5 alkyl)$_2$ in which the C1-5 alkyl may be the same or different, C2-5 alkyleneOC0-5 alkyl, C2-3 alkyleneOC1-5 fluoroalkyl, C2-3 alkyleneOC(O)C1-5 alkyl, C3-5 alkyleneNHC0-5 alkyl, C2-3 alkyleneN(C0-5 alkyl)C(O)C1-5 alkyl, C2-5 alkyleneNHaryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano, and N(C0-5 alkyl)$_2$ in which the C0-5 alkyl may be the same or different, C2-5 alkyleneNHheteroaryl, wherein said heteroaryl is a 5- or 6-membered heteroaryl, said heteroaryl being unsubstituted or substituted with a one or several independently selected C1-5 alkyl groups, C1-3 alkyleneC(O)NHC0-5 alkyl, C1-3 alkyleneC(O)N(C1-5 alkyl)$_2$ in which the C1-5 alkyl may be the same or different, C1-3 alkyleneC(O)N(C4-5 alkylene), C1-3 alkyleneC(O)OC0-5 alkyl, a 3- to 8-membered non-aromatic heterocycle, C2-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C1-3 alkylene heteroaryl, wherein said heteroaryl is a 5- or 6-membered heteroaryl, said heteroaryl being unsubstituted or substituted with a one or several independently selected C1-5 alkyl groups, C1-3 alkyleneSO$_2$C0-5 alkyl, C1-5 alkyleneSO$_3$H, aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, heteroaryl, wherein said heteroaryl is a 5- or 6-membered heteroaryl, said heteroaryl being unsubstituted or substituted with a one or several independently selected C1-5 alkyl groups, and moieties according to formula (II),

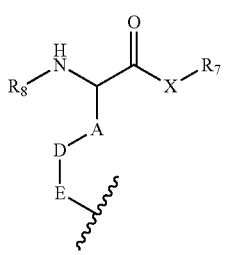

(II)

wherein the waved line indicates the point of attachment to the sulfur atom in formula (I);

A is a C1-5 alkylene;

D is a bond, a phenylene, or a heteroarylene, wherein said heteroarylene is a 5- or 6-membered heteroarylene;

E is a bond or a C1-5 alkylene;

X is NC0-C5 alkyl or "O" (oxygen);

R7 is selected from the group consisting of H, provided that X is NC0-C5 alkyl, R7 is not to be H if X is "O" (oxygen), C1-C10 alkyl, C1-5 alkyleneN(C1-5 alkyl)$_2$ in which the C1-5 alkyl may be the same or different, C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C1-3 alkylene heteroaryl, wherein said heteroaryl is a 5- or 6-membered heteroaryl, said heteroaryl being unsubstituted or substituted with a one or several independently selected C1-5 alkyl groups, an amino acid residue selected from the group consisting alanine, arginine, asparagine, aspartic acid, cysteine, glutamine, glutamic acid, glycine, histidine, isoleucine, leucine, lysine; methionine, phenylalanine, proline, threonine, tryptophan, tyrosine and valine, which amino acid residue is connected to the moiety according to formula (II) at the N-terminal of the amino acid residue and optionally esterfied at the C-terminal with a C1-5 monohydric alkanol, and a di-, a tri-, or a tetrapeptide residue, wherein the amino acid residues in said peptide residue are independently selected from the group consisting alanine, arginine, asparagine, aspartic acid, cysteine, glutamine, glutamic acid, glycine, histidine, isoleucine, leucine, lysine; methionine, phenylalanine, proline, threonine, tryptophan, tyrosine and valine, the peptide residue being connected to the moiety according to formula (II) at the N-terminal of the peptide and optionally esterfied at the C-terminal with a C1-5 monohydric alkanol; and R8 is selected from the group consisting of C(O)C1-C6 alkyl, C(O)OC1-C6 alkyl, C(O)C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C(O)C0-3 alkylene heteroaryl, wherein said heteroaryl is a 5- or 6-membered heteroaryl, said heteroaryl being unsubstituted or substituted with a one or several independently selected C1-5 alkyl groups, an amino acid residue selected from the group consisting of alanine, arginine, asparagine, aspartic acid, cysteine, glutamine, glutamic acid, glycine, histidine, isoleucine, leucine, lysine; methionine, phenylalanine, proline, threonine, tryptophan, tyrosine and valine, which amino acid residue is connected to the moiety according to formula (II) at the C-terminal of the amino acid residue, and which amino acid residue optionally is N-acylated, wherein said acyl group is selected from the group consisting C(O)C1-C6 alkyl, and C(O)C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, and a di-, a tri-, or a tetrapeptide residue, wherein the amino acid residues in said peptide residue are independently selected from the group consisting alanine, arginine, asparagine, aspartic acid, cysteine, glutamine, glutamic acid, glycine, histidine, isoleucine, leucine, lysine; methionine, phenylalanine, proline, threonine, tryptophan, tyrosine and valine, the peptide residue being connected to the moiety according to formula (II) at the C-terminal of the peptide, and the N-terminal of the peptide optionally being N-acelyated, wherein said acyl group is selected from the group consisting C(O)C1-C6 alkyl and C(O)C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different;

as a free base, an acid in its non-charged protonated form, a pharmaceutically acceptable addition salt, solvate, solvate of a salt thereof, a pure diastereomer, a pure enantiomer, a diastereomeric mixture, a racemic mixture, a scalemic mixture, a corresponding tautomeric form resulting from a hydrogen shift between two hetero-atoms and/or the corresponding tautomeric form resulting from a keto-enol tautomerization.

In compounds wherein R6 is moiety according to formula (II) and "D" represents a bond, "A" is directly connected to "E". Similarly, in compounds wherein R6 is moiety according to formula (II) and "E" represents a bond, "D" is directly connected to the sulfur atom of formula (I). In compounds wherein R6 is moiety according to formula (II) and both D" and "E" represent a bond, "A" is directly connected to the sulfur atom of formula (I) (cf. formula (IV) further below).

The individual diastereomers or enantiomers in a diastereomeric or scalemic mixture, respectively, may be present in the same amount, thus constituting a racemic mixture in the latter case, or in different amounts. However, it is preferred if one of the diastereomers or enantiomers prevails. Accordingly, its is preferred if one of the diastereomers or enantiomers is more than 50%, such as more than 75%, 90%, 95% or even more than 99%.

According to an embodiment, the compounds of the formula (I) have the relative or absolute stereochemistry according to formula (III),

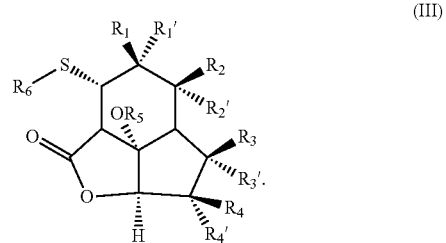

(III)

Compounds having the absolute stereochemistry according to formula (III) may be obtained by use of the natural product galiellalactone. An embodiment thus relates to compounds of the formula (I) having the absolute stereochemistry according to formula (III).

Preferably, C3-8 non-aromatic carbocycles of compounds herein are independently selected from the group consisting of cyclohexyl, cyclopentyl and cyclopropyl. Further, any heteroaryl of compounds herein are independently selected among 5-membered heteroaryls, such as thiazolyl, furanyl, thiophenyl, pyrrolyl, pyrazolyl, oxazolyl or isooxazolyl, and 6-membered heteroaryls, such as pyridyl or pyrimidinyl. In addition, 3- to 8-membered non-aromatic heterocycles of compounds herein are preferably and independently selected from the group consisting of piperidinyl, piperazinyl, morpholinyl or pyrrolidinyl. Preferably, these heterocycles are connected via a substitutable nitrogen atom. Additionally, aryls of compounds herein are preferably and independently selected among phenyl groups and naphtalenyl. When substituted, heteroaryl(s) of compounds herein are substituted at substitutable atom(s).

Preferably, any halo is fluoro, chloro or bromo.

According to an embodiment, $R_1$, $R_1'$, $R_2$, $R_2'$ $R_3$, $R_3'$, $R_4$ and $R_4'$ of a compound of formula (I) are independently selected from the group consisting of H, C1-5 alkyl, C0-5 alkyleneOC0-5 alkyl, C0-3 alkyleneNHC0-5 alkyl, C0-3 alkyleneN(C1-5 alkyl)2 in which the C1-5 alkyl may be the same or different, C0-3 alkyleneN(C0-5 alkyl)C(O)C1-5 alkyl, C0-3 alkyleneC(O)N(C1-5 alkyl)2 in which the C1-5 alkyl may be the same or different, C0-3 alkyleneC(O)OC0-5 alkyl, a 3- to 8-membered non-aromatic heterocycle, C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, and C0-3 alkylene heteroaryl. In such an embodiment, $R_1$ may be C1-5 alkyl, such as methyl, and $R_1'$, $R_2$, $R_2'$ $R_3$, $R_3'$, $R_4$ and $R_4'$ may be independently selected from the group consisting of H, C1-5 alkyl, C0-5 alkyleneOC0-5 alkyl, C0-3 alkyleneNHC0-5 alkyl, C0-3 alkyleneN(C1-5 alkyl)2 in which the C1-5 alkyl may be the same or different, C0-3 alkyleneN(C0-5 alkyl)C(O)C1-5 alkyl, C0-3 alkyleneC(O)N(C1-5 alkyl)2 in which the C1-5 alkyl may be the same or different, C0-3 alkyleneC(O)OC0-5 alkyl, a 3- to 8-membered non-aromatic heterocycle, C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, and C0-3 alkylene heteroaryl. Further, according to such an embodiment, $R_1$ may be C1-5 alkyl, such as methyl, $R_1'$, $R_2$, $R_2'$ $R_3$, $R_3'$, and $R_4'$ may all be H, and $R_4$ may be selected from the group consisting of H, C1-5 alkyl, C0-5 alkyleneOC0-5 alkyl, C0-3 alkyleneNHC0-5 alkyl, C0-3 alkyleneN(C1-5 alkyl)2 in which the C1-5 alkyl may be the same or different, C0-3 alkyleneN(C0-5 alkyl)C(O)C1-5 alkyl, C0-3 alkyleneC(O)N(C1-5 alkyl)2 in which the C1-5 alkyl may be the same or different, C0-3 alkyleneC(O)OC0-5 alkyl, a 3- to 8-membered non-aromatic heterocycle, C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, and C0-3 alkylene heteroaryl. Further, $R_5$ of a compound of formula (I) may be selected from H, C1-5 alkyl, and C(O)C1-5 alkyl. Accordingly, R5 may be H, Me, or C(O)C1-5 alkyl, such as R5 being H.

According to an embodiment, $R_1$, $R_1'$, $R_2$, $R_2'$, $R_3$, $R_3'$, $R_4$ and $R_4'$ of a compound of formula (I) are independently selected from the group consisting of H, C1-5 alkyl, halo, aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, CH$_2$aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, heteroaryl, wherein said heteroaryl is a 5- or 6-membered heteroaryl, said heteroaryl being unsubstituted or substituted with a one or several independently selected C1-5 alkyl groups, and CH$_2$heteroaryl, wherein said heteroaryl is a 5- or 6-membered heteroaryl, said heteroaryl being unsubstituted or substituted with a one or several independently selected C1-5 alkyl groups.

In some embodiments of the compound of formula (I), $R_1$ is halo; $R_1'$ is methyl; $R_2$, $R_2'$, $R_3$, and $R_3'$ are all hydrogen; $R_4$ and $R_4'$ are independently selected from the group consisting of H and phenyl; and $R_5$ preferably is H. In these embodiments, $R_1$ may be fluorine. Further, in these embodiments, $R_4$ may be H or phenyl; and $R_4'$ is hydrogen; preferably also $R_4$ is H.

According to an embodiment, $R_1$, $R_1'$, $R_2$, $R_2'$ $R_3$, $R_3'$, $R_4$ and $R_4'$ of a compound of formula (I) are independently selected from the group consisting of H, C1-5 alkyl, aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, CH$_2$aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, heteroaryl and CH$_2$heteroaryl. In such an embodiment, $R_1$ may be C1-5 alkyl, such as methyl, and $R_1'$, $R_2$, $R_2'$ $R_3$, $R_3'$, $R_4$ and $R_4'$ may be independently selected from the group consisting of H, C1-5 alkyl, aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, CH$_2$aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, heteroaryl and CH2heteroaryl. Further, according to such an embodiment, R1 may be C1-5 alkyl, such as methyl, $R_1'$, $R_2$, $R_2'$ $R_3$, $R_3'$, and $R_4'$ may all be H, and $R_4$ may be selected from the group consisting of H, C1-5 alkyl, aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, CH2aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, heteroaryl and CH2heteroaryl. In addition, $R_5$ of a compound of formula (I) may be selected from H and C1-5 alkyl. Preferably, R5 is H.

According to an embodiment, $R_1$ is C1-5 alkyl, such as methyl, $R_1'$, $R_2$, $R_2'$, $R_3$, and $R_3'$ are all H, or $R_1$ is halo, such as fluorine, $R_1'$ is C1-5 alkyl, such as methyl, $R_2$, $R_2'$, $R_3$, and $R_3'$ are all H, and $R_4$ and $R_4'$ are independently selected from the group consisting of H, C1-5 alkyl, aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, and CH2aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different. Preferably, also $R_4'$ is hydrogen in such an embodiment.

According to an embodiment, $R_2$, $R_2'$, $R_3$ and $R_3'$ of a compound of formula (I) are all H. Also $R_4$ and $R_4'$ of a compound of formula (I) may both be H. Further, one of $R_4$ and $R_4'$ may be methyl, the other being H.

According to an embodiment, $R_5$ of a compound of formula (I) may be H.

According to an embodiment, at least one of $R_1'$, $R_2$, $R_2'$, $R_3$ and $R_3'$, such as 1, 2, 3 or all 4 of $R_2$, $R_2'$, $R_3$ and $R_3'$, of a compound of formula (I) is H. Further, According to an embodiment, $R_1'$, $R_2$, $R_2'$, $R_3$, $R_3'$, $R_4$ and $R_4'$ of a compound of formula (I) are all H. Further, $R_1$ may be methyl or hydrogen, such as being methyl.

According to an embodiment at least one of $R_2$, $R_2'$, $R_3$ and $R_3'$, such as 1, 2, 3 or all 4 of $R_2$, $R_2'$, $R_3$ and $R_3'$, of a compound of formula (I) is hydrogen. Further, also $R_4$ and $R_4'$ of a compound of formula (I) may be hydrogen. In such an embodiment, $R_1$ and $R_1'$ may be selected from the group consisting of fluorine, methyl, and hydrogen. In an embodiment wherein $R_2$, $R_2'$, $R_3$, $R_3'$, $R_4$ and $R_4'$ of a compound of formula (I) all are hydrogen, $R_1$ may be fluorine and $R_1'$methyl, or $R_1$ may be methyl and $R_1'$ hydrogen.

According to an embodiment, at least one of $R_1$, $R_1'$, $R_2$, $R_2'$, $R_3$, $R_3'$, $R_4$ and $R_4'$ of a compound disclosed herein may be independently selected from the group consisting of C1-5 alkyl, aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, CH$_2$aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, heteroaryl and CH$_2$heteroaryl. Especially, in a compound of formula (I), wherein at least one of $R_1$, $R_1'$, $R_2$, $R_2'$, $R_3$, $R_3'$, $R_4$ and $R_4'$ in a compound of formula (I) is C1-5 alkyl, aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, CH$_2$aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, heteroaryl or CH2heteroaryl, at least one of $R_2$, $R_2'$, $R_3$, $R_3'$, $R_4$ and $R_4'$ of a compound disclosed herein may be independently selected from the group consisting of C1-5 alkyl, aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, CH2aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, heteroaryl and CH2heteroaryl. Further, in a compound of formula (I), wherein at least one of $R_2$, $R_2'$, $R_3$, $R_3'$, $R_4$ and $R_4'$ in a compound of formula (I) is C1-5 alkyl, aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, CH$_2$aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, heteroaryl or CH$_2$heteroaryl, at least one of $R_3$, $R_3'$, $R_4$ and $R_4'$ of a compound disclosed herein may be independently selected from the group consisting of C1-5 alkyl, aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, CH$_2$aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, heteroaryl and CH2heteroaryl. Furthermore, in a compound of formula (I), wherein at least one of $R_3$, $R_3'$, $R_4$ and $R_4'$ in a compound of formula (I) is C1-5 alkyl, aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, CH$_2$aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, heteroaryl or CH$_2$heteroaryl, at least one of $R_4$ and $R_4'$, such as $R_4$, of a compound disclosed herein may be independently selected from the group consisting of C1-5 alkyl, aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, CH2aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, heteroaryl and CH2heteroaryl. Especially, R4 may be aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, or CH2aryl, such as being phenyl.

According to an embodiment, at least one of R$_1$ and R$_1$' of a compound disclosed herein is independently selected from the group consisting of C1-5 alkyl, such as methyl, aryl, such as phenyl, CH$_2$aryl, such as benzyl, heteroaryl and CH$_2$heteroaryl. Thus, at least one of R$_1$ and R$_1$' may be C1-5 alkyl, such as methyl. Preferably, R1 is methyl in such an embodiment. Alternatively, R$_1$ is fluorine and R$_1$' is methyl.

According to an embodiment, R$_1$ and R$_1$' of a compound disclosed herein are independently selected from the group consisting of H, halo, and methyl. While both R$_1$ and R$_1$' may both be H, it's preferred for one of R$_1$ and R$_1$' to be methyl, the other one being H or fluorine. Preferably, R1 is methyl and R1' is H. Alternatively, R$_1$ may fluorine and R$_1$' methyl.

According to an embodiment, R$_1$ is methyl, R$_1$' is hydrogen, R$_2$, R$_2$', R$_3$, and R$_3$' are all hydrogen, and R$_4$ and R$_4$' are independently selected from the group consisting of H and phenyl. Further, in such an embodiment, also R$_4$' may be hydrogen. Compounds wherein also R$_4$ is hydrogen may be obtained from galiellalactone. Thus, also R$_4$ may be hydrogen. In galiellalactone R$_5$ is H. Thus, it may be preferred if R$_5$ is H. However, the tertiary hydroxyl group may be modified, such as by alkylation and acylation.

According to an embodiment, R$_1$ is fluorine, R$_1$' is methyl, R$_2$, R$_2$', R$_3$, and R$_3$' are all hydrogen, and R$_4$ and R$_4$' are independently selected from the group consisting of H and phenyl. Further, in such an embodiment, also R$_4$' may be hydrogen. Compounds wherein also R$_4$ is hydrogen may be obtained from galiellalactone. Thus, also R$_4$ may be hydrogen. In galiellalactone R$_5$ is H. Thus, it may be preferred if R$_5$ is H. However, the tertiary hydroxyl group may be modified, such as by alkylation and acylation. Compounds wherein R$_2$, R$_2$', R$_3$, R$_3$', R$_4$, R$_4$', and R$_5$ all are hydrogen, R$_1$ is fluorine, and R$_1$' is methyl may be obtained from galiellalactone.

An embodiment relates to compounds disclosed herein, wherein R$_6$ is selected from the group consisting of C1-8 alkyl, C3-C8 alkyleneN(C1-5 alkyl)$_2$ in which the C1-5 alkyl may be the same or different, C2-5 alkyleneOC0-5 alkyl, C1-3 alkyleneC(O)OC0-5 alkyl, a 3- to 8-membered non-aromatic heterocycle, C2-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C1-5 alkyleneSO3, aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, heteroaryl, wherein said heteroaryl is a 5- or 6-membered heteroaryl, said heteroaryl being unsubstituted or substituted with a one or several independently selected C1-5 alkyl groups, and moieties according to formula (II). When R$_6$ is a moiety according to formula (II):

"D" may be a bond or a phenylene, further may "E" be a bond;

R$_7$ may be selected from the group consisting of H, provided that X is NC0-C5 alkyl, R7 is not to be H if X is "O" (oxygen), C1-C10 alkyl, such as methyl, and C0-3 alkylene aryl, such as phenyl and benzyl. The aryl may be unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different; and R$_8$ may be selected from the group consisting of C(O) C1-C6 alkyl, such as C(O)Me, C(O)C0-3 alkylene aryl, such as C(O)Ph, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, and an amino acid residue selected from the group consisting alanine, glycine, isoleucine, leucine, lysine, methionine, phenylalanine, tyrosine and valine, which amino acid residue is connected to the moiety according to formula (II) at the C-terminal of the amino acid residue.

Moieties according to formula (II), wherein R$_8$ is an amino acid residue, may be represented by the following formula:

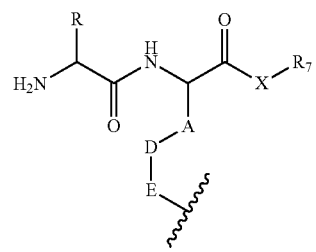

wherein R represents the substituent of the amino acid.

An embodiment relates to compounds disclosed herein, wherein —SR$_6$ comprises a cysteine residue, or an analogue to a cysteine residue, such as a homocysteine residue. In such an embodiment R$_6$ is a moiety according to formula (IV),

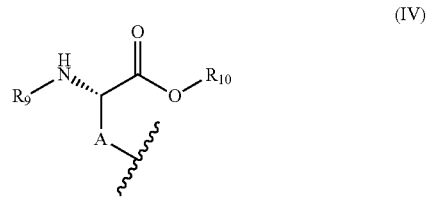

(IV)

wherein the waved line indicates the point of attachment to the sulfur atom in formula (I);

A is a C1-5 alkylene, such as methylene or ethylene;

R$_9$ corresponds to R$_8$ in formula (I); and

R$_{10}$ corresponds to R$_7$ in formula (I).

In embodiment, wherein R$_6$ is a moiety according to formula (IV), R$_9$ may be selected from the group consisting of C(O)C1-C6 alkyl, such as C(O)Me, C(O)C0-3 alkylene aryl, such as C(O)phenyl or C(O)benzyl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, and an amino acid residue selected from the group consisting alanine, glycine, isoleucine, leucine, lysine; methionine, phenylalanine, tyrosine and valine, which amino acid residue is connected to the moiety according to formula (IV) at the C-terminal of the amino acid residue, and R$_{10}$ may be selected from the group consisting of C1-C10 alkyl, such as methyl, and C0-3 alkylene aryl, such as phenyl or benzyl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different. In embodiment, wherein R$_6$ is a moiety according to formula (IV), R$_9$ may be C(O)Me.

Compounds disclosed herein may be obtained by reacting a cysteine derivative with a galiellalactone. An embodiment, thus relates to a compound according to formula (V),

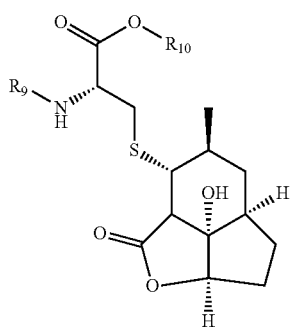

(V)

wherein R$_9$ corresponds to R$_8$ in formula (I) and R$_{10}$ corresponds to R$_7$ in formula (I). Further, R$_9$ may be selected from the group consisting of C(O)C1-C5 alkyl, such as methyl, C(O)C0-3 alkylene aryl, such as C(O)phenyl, wherein the aryl is unsubstituted or substituted with a one or several substituents independently selected from the group consisting of fluorine, chlorine and bromine, and an amino acid residue selected from the group consisting alanine, glycine, isoleucine, leucine, lysine and valine, which amino acid residue is connected to the moiety according to formula (IV) at the C-terminal of the amino acid residue. Further, R$_{10}$ may be selected from the group consisting of C1-C6 alkyl and C0-3 alkylene aryl, such as phenyl or benzyl, wherein the aryl is unsubstituted or substituted with a one or several substituents independently selected from the group consisting of fluorine, chlorine and bromine.

According to an embodiment, the compound of formula (I) is selected from the group consisting of

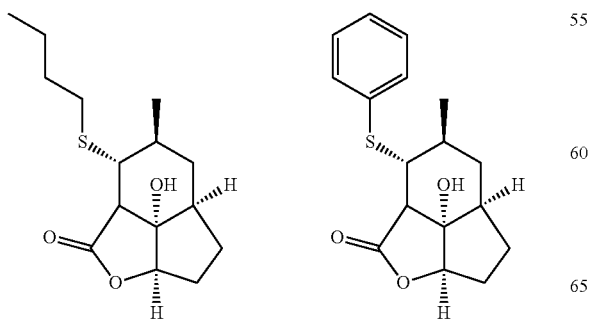

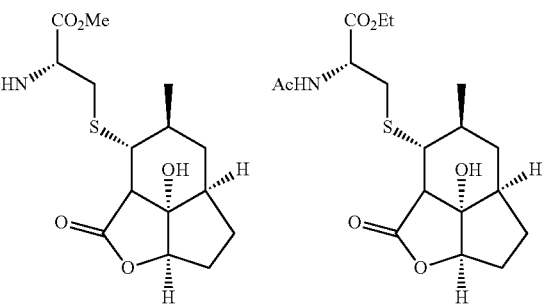

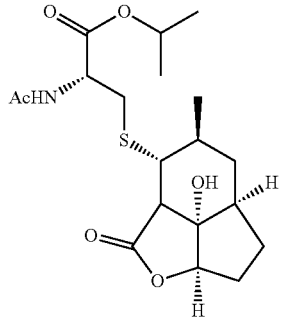

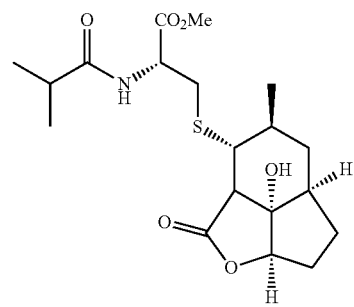

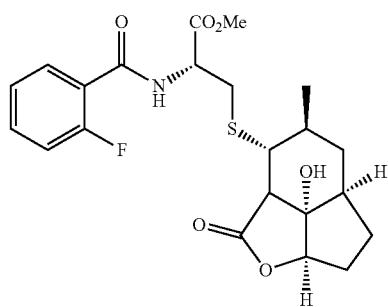

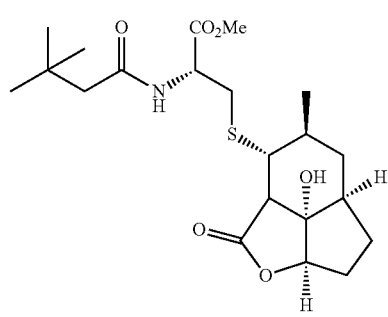

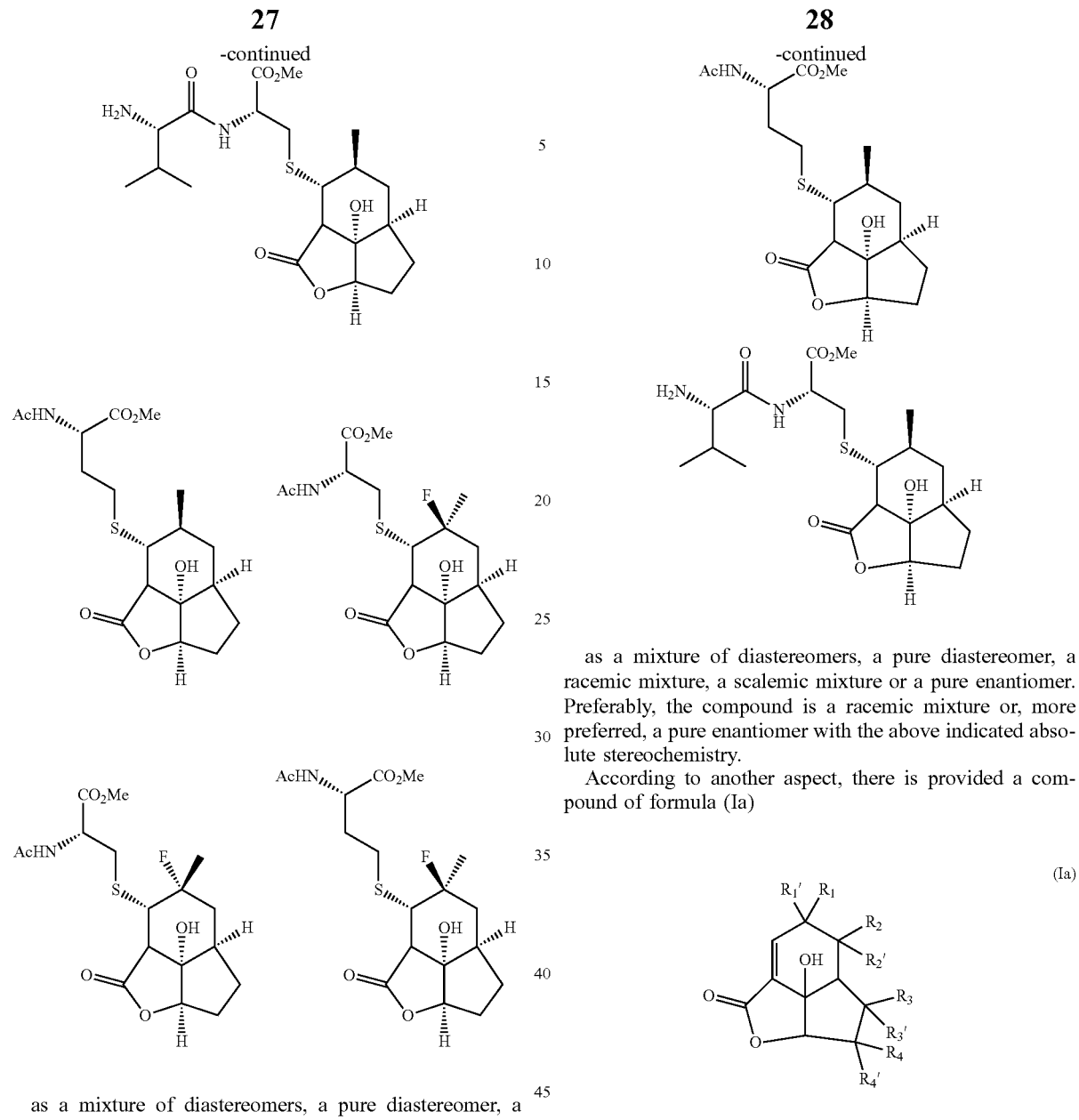

as a mixture of diastereomers, a pure diastereomer, a racemic mixture, a scalemic mixture or a pure enantiomer. Preferably, the compound is a racemic mixture or, more preferred, a pure enantiomer with the above indicated absolute stereochemistry.

According to an embodiment, the compound of formula (I) is selected from the group consisting of

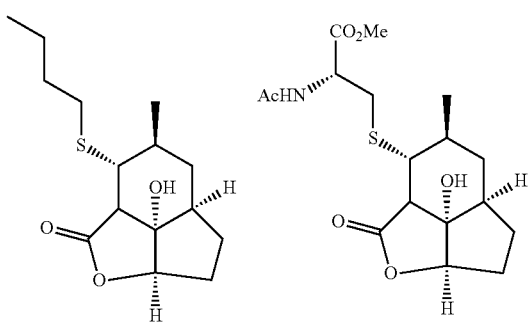

as a mixture of diastereomers, a pure diastereomer, a racemic mixture, a scalemic mixture or a pure enantiomer. Preferably, the compound is a racemic mixture or, more preferred, a pure enantiomer with the above indicated absolute stereochemistry.

According to another aspect, there is provided a compound of formula (Ia)

wherein
$R_1$ is halo;
$R_1'$ is selected from the group consisting of H, C1-5 alkyl, C1-5 fluoroalkyl, halo, C3-8 non-aromatic carbocycle, C0-5 alkyleneOC0-5 alkyl, C0-3 alkyleneOC1-5 fluoroalkyl, C0-3 alkyleneOC(O)C1-5 alkyl, OC2-3 alkyleneN(C0-5 alkyl)$_2$ in which the C0-5 alkyl may be the same or different, C0-3 alkyleneNHC0-5 alkyl, C0-3 alkyleneN(C1-5 alkyl)$_2$ in which the C1-5 alkyl may be the same or different, C0-3 alkyleneN(C0-5 alkyl)C(O)C1-5 alkyl, C0-3 alkyleneN-Haryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C0-3 alkyleneNHheteroaryl, wherein said heteroaryl is a 5- or 6-membered heteroaryl, said heteroaryl being unsubstituted or substituted with a one or several independently selected C1-5 alkyl groups, C0-3 alkyleneC(O)NHC0-5 alkyl, C0-3 alkyleneC(O)N(C1-5 alkyl)$_2$ in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C0-3 alkylene heteroaryl, wherein said heteroaryl is a 5- or 6-membered heteroaryl, said heteroaryl being unsubstituted or substituted with a one or several independently selected C1-5 alkyl groups, halo, C0-1 alkylene cyano, SC0-5 alkyl, C0-3 alkyleneSO$_2$C0-5 alkyl, nitro, C(O)C0-C5 alkyl, C(O)C1-C5 fluoroalkyl, N(C0-C3 alkyl)SO$_2$C1-C5 alkyl, and N(C0-C5 alkyl)SO$_2$C1-5 fluoroalkyl;

R$_2$ and R$_2$' are independently selected from the group consisting of H, C1-5 alkyl, C1-5 fluoroalkyl, halo, C3-8 non-aromatic carbocycle, C0-5 alkyleneOC0-5 alkyl, C0-3 alkyleneOC1-5 fluoroalkyl, C0-3 alkyleneOC(O)C1-5 alkyl, OC2-3 alkyleneN(C0-5 alkyl)$_2$ in which the C0-5 alkyl may be the same or different, C0-3 alkyleneNHC0-5 alkyl, C0-3 alkyleneN(C1-5 alkyl)$_2$ in which the C1-5 alkyl may be the same or different, C0-3 alkyleneN(C0-5 alkyl)C(O)C1-5 alkyl, C0-3 alkyleneNHaryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C0-3 alkyleneNHheteroaryl, wherein said heteroaryl is a 5- or 6-membered heteroaryl, said heteroaryl being unsubstituted or substituted with a one or several independently selected C1-5 alkyl groups, C0-3 alkyleneC(O)NHC0-5 alkyl, C0-3 alkyleneC(O)N(C1-5 alkyl)$_2$ in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C0-3 alkylene heteroaryl, wherein said heteroaryl is a 5- or 6-membered heteroaryl, said heteroaryl being unsubstituted or substituted with a one or several independently selected C1-5 alkyl groups, halo, C0-1 alkylene cyano, SC0-5 alkyl, C0-3 alkyleneSO$_2$C0-5 alkyl, nitro, C(O)C0-C5 alkyl, C(O)C1-C5 fluoroalkyl, N(C0-C3 alkyl)SO$_2$C1-C5 alkyl, and N(C0-C5 alkyl)SO$_2$C1-5 fluoroalkyl;

R$_3$ and R$_3$' are independently selected from the group consisting of H, C1-5 alkyl, C1-5 fluoroalkyl, halo, C3-8 non-aromatic carbocycle, C0-5 alkyleneOC0-5 alkyl, C0-3 alkyleneOC1-5 fluoroalkyl, C0-3 alkyleneOC(O)C1-5 alkyl, OC2-3 alkyleneN(C0-5 alkyl)$_2$ in which the C0-5 alkyl may be the same or different, C0-3 alkyleneNHC0-5 alkyl, C0-3 alkyleneN(C1-5 alkyl)$_2$ in which the C1-5 alkyl may be the same or different, C0-3 alkyleneN(C0-5 alkyl)C(O)C1-5 alkyl, C0-3 alkyleneNHaryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C0-3 alkyleneNHheteroaryl, wherein said heteroaryl is a 5- or 6-membered heteroaryl, said heteroaryl being unsubstituted or substituted with a one or several independently selected C1-5 alkyl groups, C0-3 alkyleneC(O)NHC0-5 alkyl, C0-3 alkyleneC(O)N(C1-5 alkyl)$_2$ in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C0-3 alkylene heteroaryl, wherein said heteroaryl is a 5- or 6-membered heteroaryl, said heteroaryl being unsubstituted or substituted with a one or several independently selected C1-5 alkyl groups, halo, C0-1 alkylene cyano, SC0-5 alkyl, C0-3 alkyleneSO$_2$C0-5 alkyl, nitro, C(O)C0-C5 alkyl, C(O)C1-C5 fluoroalkyl, N(C0-C3 alkyl)SO$_2$C1-C5 alkyl, and N(C0-C5 alkyl)SO$_2$C1-5 fluoroalkyl; and R$_4$ and R$_4$' are independently selected from the group consisting of H, C1-5 alkyl, C1-5 fluoroalkyl, halo, C3-8 non-aromatic carbocycle, C0-5 alkyleneOC0-5 alkyl, C0-3 alkyleneOC1-5 fluoroalkyl, C0-3 alkyleneOC(O)C1-5 alkyl, OC2-3 alkyleneN(C0-5 alkyl)$_2$ in which the C0-5 alkyl may be the same or different, C0-3 alkyleneNHC0-5 alkyl, C0-3 alkyleneN(C1-5 alkyl)$_2$ in which the C1-5 alkyl may be the same or different, C0-3 alkyleneN(C0-5 alkyl)C(O)C1-5 alkyl, C0-3 alkyleneNHaryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C0-3 alkyleneNHheteroaryl, wherein said heteroaryl is a 5- or 6-membered heteroaryl, said heteroaryl being unsubstituted or substituted with a one or several independently selected C1-5 alkyl groups, C0-3 alkyleneC(O)NHC0-5 alkyl, C0-3 alkyleneC(O)N(C1-5 alkyl)$_2$ in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C0-3 alkylene heteroaryl, wherein said heteroaryl is a 5- or 6-membered heteroaryl, said heteroaryl being unsubstituted or substituted with a one or several independently selected C1-5 alkyl groups, halo, C0-1 alkylene cyano, SC0-5 alkyl, C0-3 alkyleneSO$_2$C0-5 alkyl, nitro, C(O)C0-C5 alkyl, C(O)C1-C5 fluoroalkyl, N(C0-C3 alkyl)SO$_2$C1-C5 alkyl, and N(C0-C5 alkyl)SO$_2$C1-5 fluoroalkyl;

as a free base, an acid in its non-charged protonated form, a pharmaceutically acceptable addition salt, solvate, solvate of a salt thereof, a pure diastereomer, a pure enantiomer, a diastereomeric mixture, a racemic mixture, a scalemic mixture, a corresponding tautomeric form resulting from a hydrogen shift between two hetero-atoms and/or the corresponding tautomeric form resulting from a keto-enol tautomerization.

According to an embodiment, the compound of the formula (Ia) has the relative or absolute stereochemistry according to formula (IIIa)

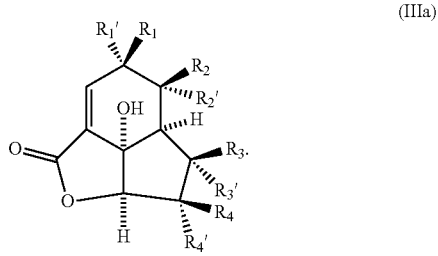

(IIIa)

According to some embodiments of the compounds of formula (Ia) or (IIIa), $R_1'$, $R_2$, $R_2'$, $R_3$, $R_3'$, $R_4$ and $R_4'$ are independently selected from the group consisting of H, C1-5 alkyl, halo, aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, CH$_2$aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, heteroaryl, wherein said heteroaryl is a 5- or 6-membered heteroaryl, said heteroaryl being unsubstituted or substituted with a one or several independently selected C1-5 alkyl groups, and CH$_2$heteroaryl, wherein said heteroaryl is a 5- or 6-membered heteroaryl, said heteroaryl being unsubstituted or substituted with a one or several independently selected C1-5 alkyl groups.

In some embodiments of the compounds of formula (Ia) or (IIIa), $R_1$ is fluorine.

According to some embodiments of the compounds of formula (Ia) or (IIIa), $R_1'$ is selected from the group consisting of H, C1-5 alkyl, C1-5 fluoroalkyl, halo, aryl, CH2aryl, heteroaryl and CH2heteroaryl.

In one embodiment of the compounds of formula (Ia) or (IIIa), $R_1'$ is C1-5 alkyl. In this embodiment, $R_1'$ may be methyl.

According to some embodiments of the compounds of formula (Ia) or (IIIa), $R_2$, $R_2'$, $R_3$, $R_3'$, $R_4$ and $R_4'$ are independently selected from the group consisting of H, C1-5 alkyl, aryl, CH2aryl, heteroaryl and CH2heteroaryl.

In some embodiments of the compounds of formula (Ia) or (IIIa), $R_2$, $R_2'$, $R_3$, $R_3'$, $R_4$ and $R_4'$ are all H.

In one particular embodiment of the compounds of formula (Ia), $R_1$ is fluorine; $R_1'$ is methyl; and $R_2$, $R_2'$, $R_3$, $R_3'$, $R_4$, and $R_4'$ are all H.

According to an embodiment, the compound of formula (Ia) is

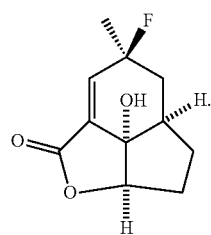

According to another aspect, there is provided a pharmaceutical composition comprising a compound according to formula (Ia) and at least one pharmaceutically acceptable carrier or excipient. Such compound of formula (Ia) and composition are useful in therapy.

According to another aspect, compounds according to formula (Ia) and compositions comprising such compounds are useful in the treatment of STAT3 signaling related disorders as well as in treatment of diseases and disorders selected from the group consisting of: solid cancers, hematological cancers, benign tumors, hyperproliferative diseases, inflammations, autoimmune diseases, graft or transplant rejections, delayed physiological function of grafts or transplants, neurodegenerative diseases and viral infections, such as from solid cancers and hematological cancers.

Without wishing to be bound by theory it is believed that including one or more halogen atoms, such as fluorine, in the tricyclic ring core of the compounds of formula (I) or (Ia) may increase the metabolic stability of the compound thus making it more resistant to metabolic degradation and resulting in a more desirable pharmacokinetic profile of the compound.

According to an embodiment, a compound of formula (I) or (Ia) may be in a crystalline form. For example, such a crystalline form may facilitate the manufacturing of a medicament comprising a compound of formula (I) or (Ia).

Although various selections, within the interval given for each of the different groups of formula (I) or (Ia), have been described individually above as various possible embodiments, any combination of these selections is also possible and thus within the scope of the present invention. Accordingly, other embodiments of the invention relates to a compound according to formula (I) or (Ia), wherein at least two different groups, such as 2, 3, 4, 5, or further different groups, of formula (I) or (Ia) are to be selected from the various selections, within the interval given for each of the different groups of formula (I) or (Ia), disclosed herein.

Compositions

Compounds disclosed herein, e.g. compounds according to formula (I) or (Ia) or preferred selections thereof, may be formulated into conventional pharmaceutical compositions, e.g. medicaments. According to an embodiment, there is thus provided a pharmaceutical composition comprising a compound as disclosed herein and at least one pharmaceutically acceptable carrier or excipient. In this context "pharmaceutically acceptable" is intended to mean an excipient or carrier that, at the dosage and concentrations employed, does not cause any unwanted effects in the patients to whom it is administered. Such pharmaceutically acceptable carriers and excipients are well-known in the art. Further, pharmaceutical composition, as described herein, may also comprise pharmaceutically diluents, stabilizers and the like.

The pharmaceutically acceptable carriers may be either solid or liquid.

Pharmaceutical compositions may typically be provided either as solid or as liquid preparations.

Solid form preparations include, but are not limited to, powders, tablets, dispersible granules, capsules, cachets, and suppositories. Powders, tablets, dispersible granules, capsules, cachets may be used as solid dosage forms suitable for oral administration, while suppositories may be used for rectal administration.

A solid carrier may be one or more substances, which may also act as diluent, flavoring agent, solubilizer, lubricant, suspending agent, binder, or tablet disintegrating agent. A solid carrier may also be an encapsulating material. Suitable carriers include, but are not limited to, magnesium carbonate, magnesium stearate, talc, lactose, sugar, pectin, dextrin, starch, tragacanth, methyl cellulose, sodium carboxymethyl cellulose, low-melting wax, cocoa butter, and the like.

In powders, the carrier is normally a finely divided solid, which is in a mixture with the compound as disclosed herein, also typically being finely divided. In tablets, the active component may be mixed with the carrier having the necessary binding properties in suitable proportions and compacted in the shape and size desired.

For preparing suppository compositions, a low-melting wax, such as a mixture of fatty acid glycerides and cocoa butter, may first be melted and the active ingredient, like a compound of the invention, may then be dispersed therein by, for example, stirring. The molten homogeneous mixture may then be poured into convenient sized moulds and allowed to cool and solidify.

The term composition is also intended to include the formulation of the active component with encapsulating material as a carrier providing a capsule in which the active component (with or without other carriers) is surrounded by a carrier which is thus in association with it. Similarly, cachets are included.

Liquid form preparations include, but are not limited to, solutions, suspensions, and emulsions. For example, dissolvation or dispersion of the compounds disclosed herein in sterile water or mixture of water and propylene glycol may provide liquid preparations suitable for parenteral administration. Liquid compositions may also be formulated in solution in aqueous polyethylene glycol solution.

Aqueous solutions for oral administration may be prepared by dissolving the active component, like a compound of the invention, in water and adding suitable colorants, flavoring agents, stabilizers, and thickening agents as desired. Aqueous suspensions for oral use may be made by dispersing the finely divided active component in water together with a viscous material such as natural synthetic gums, resins, methyl cellulose, sodium carboxymethyl cellulose, and other suspending agents known to the pharmaceutical formulation art. Exemplary compositions intended for oral use may contain one or more coloring, sweetening, flavoring and/or preservative agents.

A pharmaceutical composition according to embodiments disclosed herein may be administered through different routes such as, but not limited to, intravenously, intraperitonealy, intramuscularly, intranasaly, subcutaneously, sublingually, rectally, orally as well as through inhalation or insufflation.

Depending on the mode of administration, the pharmaceutical composition may include from about 0.05 wt % (percent by weight) to about 99 wt %, such as about 0.10 wt % to about 50 wt %, about 0.5 wt % to about 30, or about 1.0 wt % to about 25 wt %, of a compound disclosed herein, all percentages by weight being based on the total weight of the composition.

Therapy

Compounds disclosed herein, e.g. compounds according to formula (I) or (Ia) or preferred selections thereof, as well as pharmaceutical compositions comprising such a compounds, may be used for the treatment of various diseases or conditions in humans or mammals, such as dogs, cats, horses, cows or other mammals; in particular domestic mammals. Mammals may be treated for the same diseases and conditions as humans may be treated for.

When used in therapy, a pharmaceutical composition according embodiments herein may be administered to the patient in a pharmaceutically effective dose. By "pharmaceutically effective dose" is meant a dose that is sufficient to produce the desired effects in relation to the condition for which it is administered. The exact dose may be dependent on the activity of the compound, manner of administration, nature and severity of the disorder and/or disease and the general conditions, such as age and body weight of the patient.

A therapeutically effective amount for the practice of the present invention may be determined by one of ordinary skill in the art using known criteria including the age, weight and response of the individual patient, and interpreted within the context of the disease which is being treated or which is being prevented.

Treatment of STAT3 Signaling Related Disorder and Inhibition of Proliferation of Cancer Cells The parent compound galiellalactone and related compounds (cf. WO 2012/010555) are covalent inhibitors of STAT3, binding directly to STAT3 and preventing DNA binding. As described herein above, the transcription factor STAT3 has emerged as a highly promising target for the treatment of various cancers, e.g. castration resistant prostate cancer (CRPC). In CRPC, constitutive activation of STAT3 is implicated in drug resistance, the progression of androgen independent growth, metastasis, immune avoidance and tumor growth.

Galiellalactone has indeed been found to inhibit proliferation of DU145 prostate cancer cells (cf. Hellsten et al; Prostate 68; 269-280, 2008). Without being bound to any theory, it is believed that Galiellalactone induces apoptosis by down regulating STAT3 related genes.

As the compounds disclosed herein are rapidly absorbed and converted to the parent compound, being a Michael acceptor, e.g. galiellalactone, when administered orally, they may be used to treatment or prevention of a STAT3 signaling related disorder. Further, independently if exerted via their effect on STAT3 signaling or not, compounds disclosed herein may be used in the treatment of cancer, as they inhibit proliferation of cancer cells.

An embodiment thus relates to compounds and pharmaceutical compositions disclosed herein, e.g. compounds according to formula (I) or (Ia) or preferred selections thereof, for use in treatment or prevention of a STAT3 signaling related disorder. Examples of STAT3 signaling related disorders include various cancers, such as solid cancers and hematological cancer, benign tumors, hyperproliferative diseases, inflammation, autoimmune diseases, graft or transplant rejections, delayed physiological function of grafts or transplants, neurodegenerative diseases or viral infections.

In addition to the effect on STAT3, galiellalactone has also been shown to block TGF-beta signaling (Rudolph et al Cytokine. 2013 January; 61(1):285-96) and to be effective in an in vivo murine model of allergic asthma (Hausding et al Int Immunol. 2011 January; 23(1):1-15).

Irrespectively of interfering with STAT3 signaling or not, compounds and pharmaceutical compositions disclosed herein may be used in the treatment or prevention of cancer. Another embodiment thus relates to compounds and pharmaceutical compositions disclosed herein for use in the prevention or treatment of cancer, such as solid cancers or hematological cancers.

Examples of solid cancers include, but are not limited to, sarcomas, breast cancer, prostate cancer, head and neck cancer, brain tumors, colorectal cancer, lung cancer, pancreatic cancer, cervical cancer, ovarian cancer, melanoma, gastric cancers, renal cell carcinoma, endometrial cancer, sarcomas and hepatocellular carcinomas. Examples hematological cancers include, but are not limited to, chronic myelogenous leukemia, acute myelogenous leukemia, cutaneous T-cell lymphoma, Hodgkin's disease, anaplastic large-cell lymphoma and Burkitt's lymphoma.

Further, the cancers to be treated by compounds and pharmaceutical compositions disclosed herein, are according to an embodiment selected from the group consisting of leukemia, lymphomas, multiple myeloma, breast cancer, prostate carcinoma, lung cancer (non-small-cell), renal cell carcinoma lung cancer, hepatocellular carcinoma, cholangiocarcinoma, ovarian carcinoma, pancreatic adenocarcinoma, melanoma, head and neck squamous cell carcinoma.

Irrespectively if interfering with STAT3 signaling or not, compounds and pharmaceutical compositions disclosed herein may be used in the treatment or prevention of benign tumors. Another embodiment thus relates to compounds and pharmaceutical compositions disclosed herein for use in the prevention or treatment of benign tumors, including for example Cardiac myxoma and Castleman's disease.

Compounds and pharmaceutical compositions disclosed herein may inhibit proliferation or angiogenesis, induces apoptosis, sensitizes to apoptosis or causes cytotoxicity of cancer cells, including cancer stem cells e.g. leukemic, prostate and breast cancer stem cells. Preferably, the cancer displays elevated or aberrant STAT3 signaling or activity, constitutively phosphorylated or active STAT3 or increased STAT3 protein expression. According to an embodiment, compounds and pharmaceutical compositions disclosed herein are thus used to inhibit the growth or migration of cells. These cells may have elevated or aberrant STAT3 signaling or activity, constitutively phosporylated or active STAT3 or increased STAT3 protein expression. Hence, associated diseases and disorders, such as hyperproliferative diseases, may be treated or prevented by use of compounds and pharmaceutical compositions disclosed herein. Another embodiment thus relates to compounds and pharmaceutical compositions disclosed herein for use in the prevention or treatment hyperproliferative diseases.

IL-6 often is often involved in STAT3 signaling. Independently of involving effects or not of STAT3 signaling, compounds and pharmaceutical compositions disclosed herein may be used for treatment or prevention of IL-6 mediated inflammation and/or autoimmune diseases and disorders, such as diseases and disorders related to the production of acute phase proteins. Another embodiment thus relates to compounds and pharmaceutical compositions disclosed herein for use in the prevention or treatment of IL-6 mediated inflammation and/or autoimmune diseases and disorders. Such diseases and disorders include, but are not limited to, atherosclerosis, diabetes type 2, dementia, osteoporosis, hypertension, coronary artery disease.

According to an embodiment, compounds and pharmaceutical compositions disclosed herein are used for the prevention or treatment of inflammatory and/or autoimmune diseases including, but not limited to, arthritis, Crohn's disease, ulcerative colitis, rheumatoid arthritis, inflammatory bowel diseases, asthma, allergy, e.g. Atopic dermatitis, systemic lupus erythematosus, uveitis and COPD. In addition, compounds of the invention may be used for the suppression of graft and transplant rejection, or for improved onset of the physiological functions of such grafts and transplants after transplantation.

According to an embodiment, compounds and pharmaceutical compositions disclosed herein are used for the prevention or treatment of inflammatory, autoimmune and neurodegenerative diseases affecting the CNS including, but not limited to, Parkinson's disease, Alzheimer's disease, multiple sclerosis, stroke and ischemia reperfusion injury.

According to an embodiment, compounds and pharmaceutical compositions disclosed herein are used for the prevention or treatment of chronic viral infections including, but not limited to, hepatitis C, herpes, infections caused by Kaposis Sarcoma-associated herpes virus (KSHV) and Epstein-Barr virus related infections.

According to an embodiment, compounds and pharmaceutical compositions disclosed herein are prevention or treatment of hyperproliferative diseases including, but not limited to, psoriasis.

When used in therapy, a pharmaceutical composition according embodiments herein may be administered to the patient in a pharmaceutically effective dose. By "pharmaceutically effective dose" is meant a dose that is sufficient to produce the desired effects in relation to the condition for which it is administered. The dose required for the therapeutic or preventive treatment of a particular disease or disorder will necessarily be varied depending on the host treated, the route of administration and the severity of the illness being treated. Further, the exact dose may be dependent on the activity of the compound, manner of administration, nature and severity of the disorder and/or disease and the general conditions, such as age and body weight of the patient.

A therapeutically effective amount for the practice of the present invention may be determined by one of ordinary skill in the art using known criteria including the age, weight and response of the individual patient, and interpreted within the context of the disease which is being treated or which is being prevented.

Evidently, compounds and pharmaceutical compositions disclosed herein may used for the manufacture of a medicament for use in such treatment and prevention as disclosed herein.

Similarly, compounds and compositions disclosed herein may obviously also be used in method for treating or preventing such diseases and disorders as have been disclosed herein. Such a method includes the step of administering an effective amount of the compound, or the pharmaceutical composition, to a subject in need for such treatment.

In the context of the present specification, the term "therapy" and "treatment" includes prevention or prophylaxis, unless there are specific indications to the contrary. The terms "therapeutic" and "therapeutically" should be construed accordingly.

According to an embodiment, treatment does also encompass pre-treatment, i.e. prophylactic treatment.

When used herein, "prevent/preventing" should not be construed to mean that a condition and/or a disease never might occur again after use of a compound or pharmaceutical composition according to embodiments disclosed herein to achieve prevention. Further, the term should neither be construed to mean that a condition not might occur, at least to some extent, after such use to prevent said condition. Rather, "prevent/preventing" is intended to mean that the condition to be prevented, if occurring despite such use, will be less severe than without such use.

Combination Therapy

As already described, pharmaceutical composition as disclosed herein may be used in therapy, the disclosed compounds, e.g. compounds according to formula I or preferred selections thereof, acting as the principal therapeutic agent.

However, the disclosed compound may also be supplemented with additional therapeutically active agent(s). According to an embodiment, the pharmaceutical composition does comprise one or more additional therapeutic agent(s). Preferably, the one or more additional therapeutic agents are selected among therapeutic agents having a mechanism of action that differ from the mechanism of action of the compound disclosed herein. An advantageous synergistic effect between the therapeutic agent and the compound disclosed herein may then occur, allowing a more effective combat of e.g. a disease than if only such a therapeutic agent or a compound as disclosed herein is used. The additional therapeutic agent may be an anti-cancer agent, e.g. chemotherapeutic agents. Further, also other therapeutic agents well known in the art, being effective for other diseases and conditions as described herein, may advantageously be used in combination with a compound as disclosed herein, in order to e.g. achieve a synergistic effect.

According to an embodiment, a compound or a pharmaceutical composition as disclosed herein is used in combination with other treatments or therapies, in particular cancer therapies, including chemotherapy, radiation therapy, gene therapy, cell therapy and surgery. As an example, compounds disclosed herein may enhance anti-tumor immune mediated cytotoxicity. Hence, synergistic effects between a compound disclosed herein, and another treatment or therapy or an immune mediated response, may favorably occur.

According to an embodiment, a pharmaceutical composition according to embodiments herein may be administered alone or in combination with other therapeutic agents. These agents may be incorporated as part of the same pharmaceutical composition or may be administered separately. It is well known in the art that a combination of mechanistically unrelated therapeutic agents in the same medicament may have beneficial effects in the treatment of conditions or diseases characterized by e.g. abnormal immune regulation, abnormal hematopoiesis, inflammation or oncogenesis.

Examples of other therapeutic agents include, but is not limited to, anti-cancer agents such as Abraxane, Abiraterone, Aldesleukin, Alemtuzumab, Aminolevulinic Acid, Anastrozole, Aprepitant, Arsenic Trioxide, Azacitidine, Bendamustine Hydrochloride, Bevacizumab, Bexarotene, Bortezomib, Bleomycin, Cabazitaxel, Capecitabine, Carboplatin, Cetuximab, Cisplatin, Clofarabine, Cyclophosphamide, Cytarabine, Dacarbazine, Dasatinib, Daunorubicin Hydrochloride, Decitabine, Degarelix, Denileukin Diftitox, Dexrazoxane Hydrochloride, Docetaxel, Doxorubicin Hydrochloride, Doxorubicin Hydrochloride Liposome, Eltrombopag Olamine, Enzalutamide, Epirubicin Hydrochloride, Erlotinib Hydrochloride, Etoposide, Etoposide Phosphate, Everolimus, Exemestane, Filgrastim, Fludarabine Phosphate, Fluorouracil, Fulvestrant, Gefitinib, Gemcitabine Hydrochloride, Ibritumomab Tiuxetan, Imatinib Mesylate, Imiquimod, Irinotecan Hydrochloride, Ixabepilone, Lapatinib Ditosylate, Lenalidomide, Letrozole, Leucovorin Calcium, Leuprolide Acetate, Liposomal Cytarabine, Methotrexate, Nelarabine, Nilotinib, Ofatumumab, Oxaliplatin, Paclitaxel, Palifermin, Palonosetron Hydrochloride, Panitumumab, Pazopanib Hydrochloride, Pegaspargase, Pemetrexed Disodium, Plerixafor, Pralatrexate, Raloxifene Hydrochloride, Rasburicase, Recombinant HPV Bivalent Vaccine, Recombinant HPV Quadrivalent Vaccine, Rituximab, Romidepsin, Romiplostim, Sipuleucel-T, Sorafenib Tosylate, Sunitinib Malate, Talc, Tamoxifen Citrate, Tasquinimod, TAK700, Temozolomide, Temsirolimus, Thalidomide, Topotecan Hydrochloride, Toremifene, Tositumomab and I 131 Iodine Tositumomab, Trastuzumab, Vincristine Sulfate, Vorinostat, ARN-509, ODM-201, custirsen, AT 101, cisplatin, abozantinib, dasatinib, MK2206, axitinib, saracatinib, tivantinib, linsitinib, GSK2636771, BKM120, Vorinostat, panobinostat, azacitidine, IPI-504, STA9090, lenalidomid, OGX-427, Zoledronic Acid and Xofigo, or the like.

When a compound according to embodiments disclosed herein is combined with at least another therapeutic agent, such as an anti-cancer agent, in a pharmaceutical composition, such as a medicament, a therapeutically effective dose of the pharmaceutical composition may comprise 1 to 10 times less than the respective established therapeutically effective dose of a component, i.e. a compound according to the invention or the therapeutic agent, when administered alone for prevention or treatment of the same disease or condition.

Accordingly, by combining a compound according to embodiments disclosed herein with another therapeutic agent, such as an anti-cancer agent, it may be possible to achieve synergistic effects compared to if only a compound according to the present invention, or the other therapeutic agent, were administrated alone.

For example compounds as disclosed herein, e.g. compounds according to formula I, may be used for reversing drug resistance and/or enhancing effects of anti cancer agents, thus offering the possibility of lowering the dose of the anticancer agent to avoid side-effects and/or enhancing the efficacy.

Pharmacological Tools

According to an embodiment, compounds disclosed herein are useful as pharmacological tools in the development and standardization of in-vitro and in-vivo test systems for the evaluation of other compounds with similar activity. Such in-vivo test systems include tests in laboratory animals such as cats, dogs, rabbits, monkeys, pigs, goats, guinea pigs, rats and mice. Furthermore, compounds disclosed herein may be used as molecular probes to identify and/or locate the target of their action, such as targets of relevance for STAT3 signaling, as well as employed as a diagnostic tool for diagnosis of a disease or condition in-vivo, ex-vivo or in-vitro, or as synthetic precursors to such probes.

Molecular probes are based on compounds disclosed herein, wherein one or several of the composing atoms have been enriched with a radioactive or by other means detectable isotope, and fluorescent compounds as well known to the one skilled in the art. Hence, compounds disclosed herein may include compounds wherein one or several atoms have been substituted with heavier isotopes, such as substitution of hydrogen for deuterium, carbon-12 for carbon-13 or carbon-14, and/or nitrogen-14 for nitrogen-15.

Although the present invention has been described above with reference to specific illustrative embodiments, it is not intended to be limited to the specific form set forth herein. Any combination of the above mentioned embodiments should be appreciated as being within the scope of the invention. Rather, the invention is limited only by the accompanying claims and other embodiments than the specific above are equally possible within the scope of these appended claims.

In the claims, the term "comprises/comprising" does not exclude the presence of other species or steps. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality Methods of Preparation Another embodiment relates to a process for preparing a compound disclosed herein, e.g. compounds according to formula (I) or (Ia) or preferred selections thereof, as a free base, acid, or salts thereof. Further, additionally embodiments relate to synthetic intermediates, which are useful in the synthesis of a compound of formula (I) as a free base, acid, or salts thereof. Specific and generic examples of such intermediates are given below. Further, such intermediates may include compounds according to formula (I), which may be used to produce another compound according to formula (I).

Throughout the following description of such processes it is to be understood that, where appropriate, suitable protecting groups will be attached to, and subsequently removed from, the various reactants and intermediates in a manner that will be readily understood by one skilled in the art of organic synthesis. Conventional procedures for using such protecting groups, as well as examples of suitable protecting groups, are well known within the art. Further such procedures and groups are described in the literature, such as in "Protective Groups in Organic Synthesis", 3rd ed., T. W. Green, P. G. M. Wuts, Wiley-Interscience, New York (1999).

It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to the one skilled in the art of organic synthesis.

Examples of transformations are given below, and it is to be understood that the described transformations are not limited only to the generic groups or substituents for which the transformations are exemplified.

References and descriptions on other suitable transformations are for example given in "Comprehensive Organic Transformations—A Guide to Functional Group Preparations", 2nd ed., R. C. Larock, Wiley-VCH, New York (1999). References and descriptions of other suitable reactions are described in textbooks of organic chemistry well known to the one skilled in the art, such as "March's Advanced Organic Chemistry", 5th ed., M. B. Smith, J. March, John Wiley & Sons (2001) or, "Organic Synthesis", 2nd ed., M. B. Smith, McGraw-Hill, (2002).

In the various schemes given below, generic groups, such as R-groups, have the same representation as given above herein, if not specifically defined.

Methods of Preparation of Final Compounds of Formula (I) by the Reaction Between Intermediates (VI) and (VII) (Scheme 1)

Scheme 1

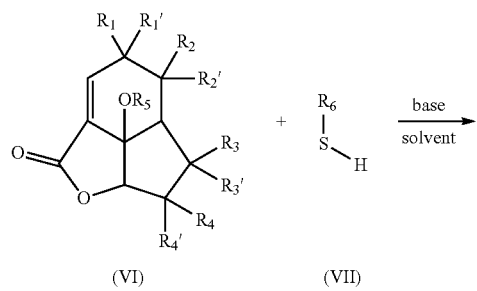

(VI)    (VII)

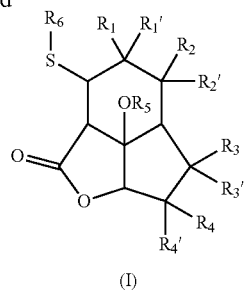

(I)

Products of structure (I) maybe prepared by reacting structures of (VI) with thiols (VII) through a conjugate addition in the presence of a suitable base or acid as catalyst or in stoichiometric amounts.

Methods of Preparation of Final Compounds of Formula (I) by the Reaction Between Intermediates (VI) and (VIII) (Scheme 2)

Scheme 2

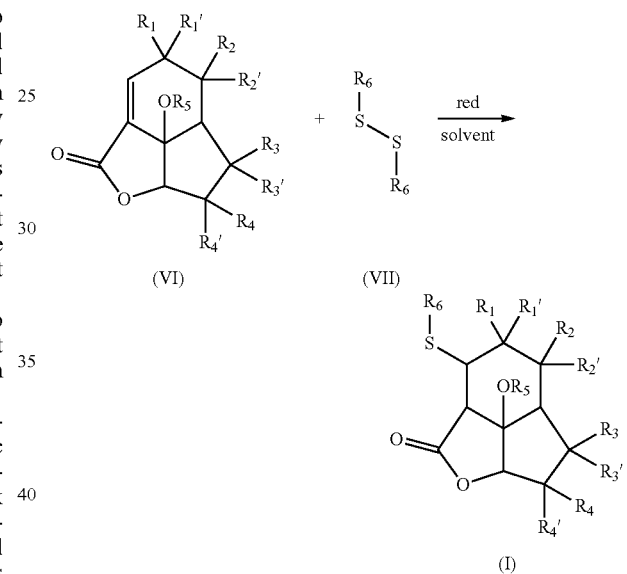

(VI)    (VII)

(I)

Products of structure (I) maybe prepared by reacting structures of (VI) with in situ generated thiols through a conjugate addition in the presence of a suitable base or acid as catalyst or in stoichiometric amounts. The in situ generated thiols are formed by reducing the corresponding disulfide (VIII) with an appropriate reducing agent e.g. NaBH$_4$, PPh$_3$, P(nBu)$_3$.

Methods of Preparation of Final Compounds of Formula (I) by the Reaction Between Intermediates (II) and (V) (Scheme 3)

Scheme 3

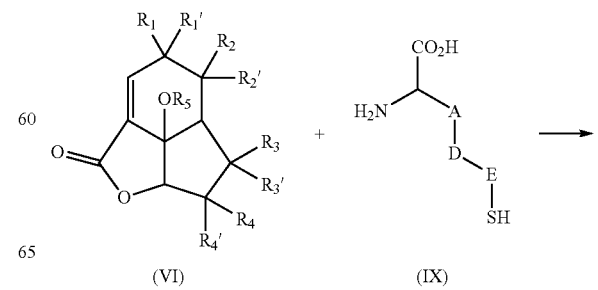

(VI)    (IX)

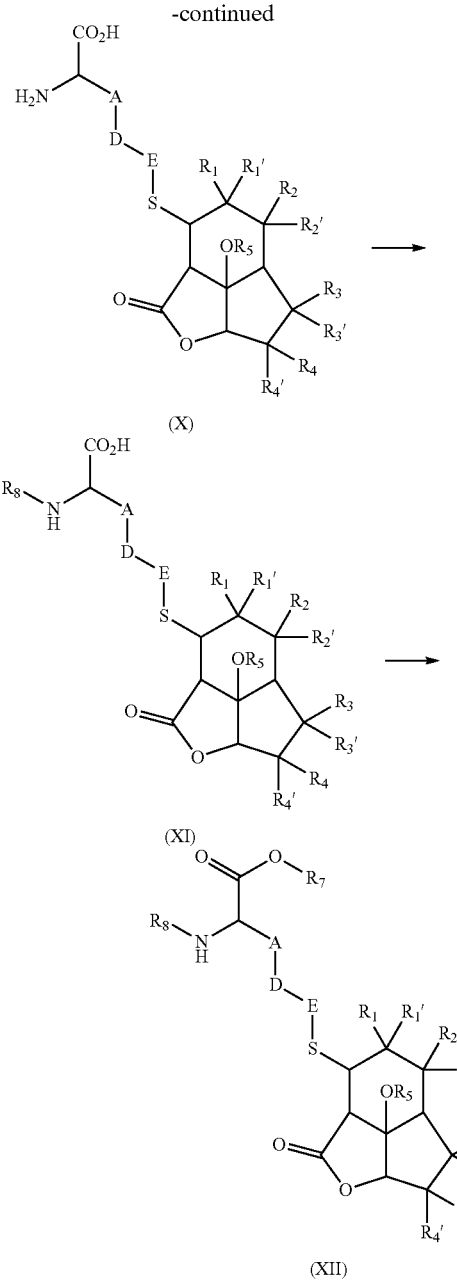

(X)

(XI)

(XII)

Products of structure (XII) maybe prepared by reacting structures of (VI) with amino acid thiols (IX) through a conjugate addition in the presence of a suitable base or acid as catalyst or in stoichiometric amounts. The intermediate amino acid (X) can be alkylated or acylated on the free nitrogen group to obtain intermediates of structure (XI). These carboxylic acids can be esterified using known methods, e.g. converting (XI) to an acid chloride or using activating reagents, to give final compounds of structure (XII).

Methods of preparation of intermediate compounds of formula (VII) and (VIII) are described in e.g. Rayner, C. M. Contemp. Org. Synth., 1995, 2, 409-440.

The synthesis of intermediates of structure (II) are described in WO 2012/010555, WO 2012/011864, Org Lett. 2010 12(22), 5100-3 and J Antibiot 2002 55(7), 663-5

EXPERIMENTAL

Abbreviations

TEA Triethyl amine
Boc t-Butyloxycarbonyl
eq Equivalent

COMPOUND EXAMPLES

Preparation of Intermediates

Below follows non-limiting examples on the synthesis of intermediates useful for the preparation of compounds of formula (I).

Preparation of Final Compounds

Below follows non-limiting examples on the synthesis of final compounds of formula I.

General Methods

All materials were obtained from commercial sources and were used without further purification unless otherwise noted. THF was distilled from sodium and benzophenone. NMR spectra (in $CDCl_3$, $CD_3OD$ or DMSO-d6) were recorded on a Bruker DRX 400 or on a Bruker Ultrashield 400 spectrometer at 400 MHz. All chemical shifts are in ppm on the delta-scale ($\delta$) relative to TMS using the residual $CHCl_3$ peak in $CDCl_3$, or the residual $CD_2HOD$ peak in $CD_3OD$, or the residual $CD_3SOCD_2H$ peak in $(CD_3)_2SO$ as internal standard (7.26, 3.31 or 2.50 ppm respectively relative to TMS) and the fine splitting of the signals as appearing in the recordings (s: singlet, d: doublet, t: triplet, q: quartet, m: multiplet, br: broad signal). Flash chromatography was performed using 60 Å 35-70 μm Davisil silica gel. TLC analyses were made on Silica Gel 60 F254 (Merck) plates and visualised under a 254/365 nm UV-lamp.

Techniques for purification of intermediates and final products include for example, straight and reversed phase chromatography on column or rotating plate, size exclusion chromatography, recrystallisation, distillation and liquid-liquid or solid-liquid extraction, which will be readily understood by the one skilled in the art.

The terms "room temperature" and "ambient temperature" shall mean, unless otherwise specified, a temperature between 16 and 25° C. The term "reflux" shall mean, unless otherwise stated, in reference to an employed solvent using a temperature at or slightly above the boiling point of the named solvent. It is understood that microwaves can be used for the heating of reaction mixtures.

The terms "flash chromatography" or "flash column chromatography" shall mean preparative chromatography on silica using an organic solvent, or mixtures thereof, as mobile phase.

Scheme 4

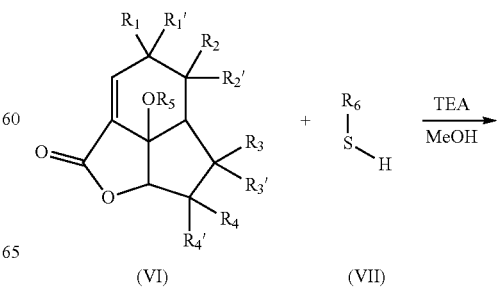

(VI)  (VII)

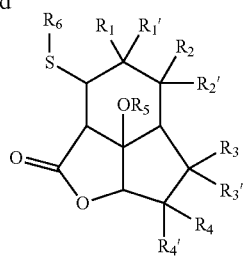

(I)

General Procedure for the Conjugate Addition of Thiols to (Scheme 4)

0.17 mmol 1.0 eq (VI) was dissolved in 2 ml MeOH and the thiol 0.18 mmol 1.1 eq (VII) was added followed by 0.017 mmol TEA 0.1 eq. The reaction mixture was stirred over night and concentrated under reduced pressure. The product (I) was purified using flash chromatography (solvent system, yield and analytical data are given for each compound).

Example 1

3β-(Butylthio)-2aβ,3-dihydrogaliellalactone

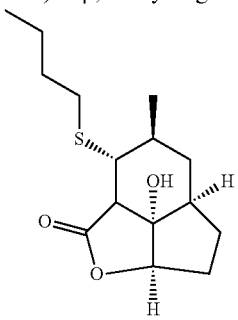

(heptane/EtOAc 7:3)
Yield: 72%
$^1$H NMR (CDCl$_3$) δ 4.59 (m, 1H), 3.20 (m, 1H), 3.06 (m, 1H), 2.65 (s, 1H), 2.61 (m, 2H), 2.23 (m, 1H), 2.12 (m, 1H), 2.08 (m, 1H), 2.00 (m, 1H), 1.78 (m, 1H), 1.64 (m, 1H), 1.63 (m, 2H), 1.51 (m, 1H), 1.43 (m, 2H), 1.15 (d, 3H), 0.93 (m, 3H), 0.78 (m, 1H).
HRMS: calc for C17H25O3S (M+H) 285.1524. found 285.1524.

Example 2

3β-(Phenylthio)-2aβ,3-dihydrogaliellalactone

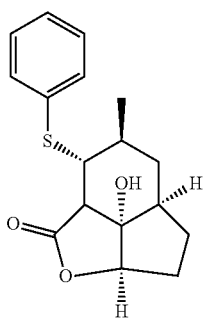

(heptane/EtOAc 7:3)
Yield: 72%
$^1$H NMR (CDCl$_3$) δ 7.45 (m, 2H), 7.34 (m, 2H), 7.25 (m, 1H), 4.50 (m, 1H), 3.63 (m, 1H), 3.15 (m, 1H), 2.39 (s, 1H), 2.25 (m, 1H), 2.15 (m, 1H), 2.06 (m, 1H), 2.00 (m, 1H), 1.84 (m, 1H), 1.75 (m, 1H), 1.51 (m, 1H), 1.22 (d, 3H), 0.85 (m, 1H).
HRMS: calc for C17H21O3S (M+H) 305.1211. found 305.1219.

Example 3

3β-(N-acetyl L-cysteine methyl ester)-2aβ,3-dihydrogaliellalactone

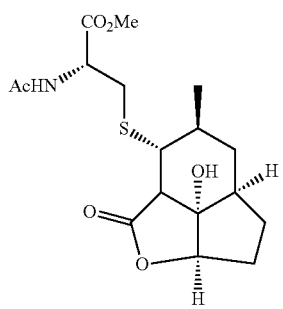

(EtOAc 100%)
Yield: 62%
$^1$H NMR (CDCl$_3$) δ 6.50 (d, 1H), 4.90 (m, 1H), 4.60 (m, 1H), 3.81 (s, 3H), 3.43 (m, 1H), 3.08 (m, 2H), 3.02 (m, 1H), 2.21 (m, 1H), 2.11 (m, 1H), 2.08 (s, 3H) 2.03 (m, 2H), 1.85 (m, 1H), 1.57 (m, 1H), 1.42 (m, 1H), 1.13 (d, 3H), 0.74 (m, 1H).
HRMS: calc for C17H26NO6S (M+H) 372.1481. found 372.1499.

Example 4

3β-(N-acetyl L-cysteine ethyl ester)-2aβ,3-dihydrogaliellalactone

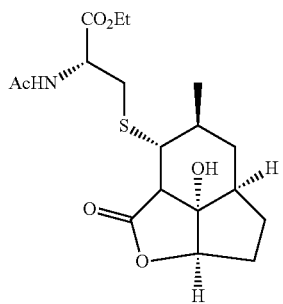

(EtOAc 100%)
Yield: 44%
$^1$H NMR (CDCl$_3$) δ 6.59 (d, 1H), 4.86 (dd, 1H), 4.59 (t, 1H), 4.25 (m, 2H), 3.41 (m, 1H), 3.08 (m, 2H), 3.00 (m, 1H), 2.20 (m, 1H), 2.10 (m, 1H), 2.02 (s, 3H), 2.02 (m, 2H), 1.85 (m, 1H), 1.59 (m, 2H) 1.32 (t, 3H), 1.12 (d, 3H), 0.73 (m, 1H).

HRMS: calc for C18H28NO6S (M+H) 386.1637. found 386.1623.

Example 5

3β-(N-pivaloyl L-cysteine methyl ester)-2aβ,3-dihydrogaliellalactone

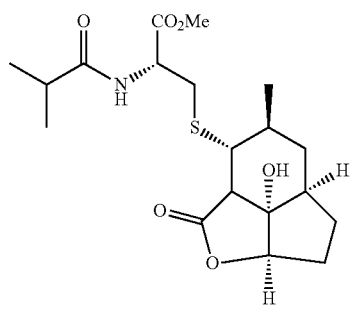

(Heptane/EtOAc 2:3)

Yield: 72%

¹H NMR (CDCl₃) δ 6.52 (d, 1H), 4.85 (m, 1H), 4.59 (m, 1H), 3.79 (s, 3H), 3.47 (m, 1H), 3.06 (m, 2H), 2.99 (m, 1H), 2.47 (m, 1H), 2.19 (m, 1H), 2.09 (m, 1H), 2.01 (m, 2H), 1.84 (m, 1H), 1.57 (m, 1H), 1.39 (m, 1H), 1.18 (d, 3H), 1.16 (d, 3H), 1.11 (d, 3H), 0.71 (m, 1H).

HRMS: calc for C19H30NO6S (M+H) 400.1794. found 400.1780.

Example 6

3β-(N-(tert-butylcarbonate)-L-cysteine methyl ester)-2aβ,3-dihydrogaliellalactone

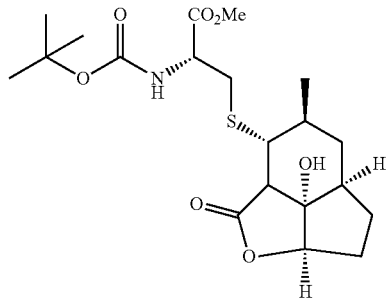

(Heptane/EtOAc 7:3)

Yield: 70%

¹H NMR (CDCl₃) δ 5.48 (d, 1H), 4.57 (m, 1H), 4.56 (d, 1H), 3.78 (s, 3H), 3.37 (m, 1H), 3.05 (m, 2H), 3.01 (m, 1H), 2.20 (m, 1H), 2.09 (m, 1H), 2.02 (m, 2H), 1.82 (m, 1H), 1.59 (m, 1H), 1.44 (s, 9H), 1.12 (d, 3H), 0.73 (m, 1H).

HRMS: calc for C20H31NO7SNa (M+Na) 452.1719. found 452.1736.

Example 7

3β-(N-acetyl L-cysteine amide)-2aβ,3-dihydrogaliellalactone

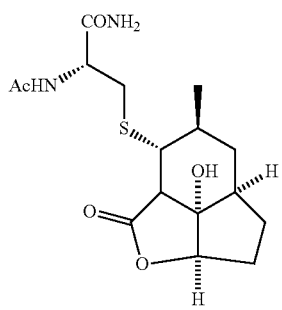

(CHCl₃/MeOH 9:1+3% acetic acid)

Yield: 65%

¹H NMR (CDCl₃) δ 7.21 (d, 1H), 4.82 (m, 1H), 4.61 (m, 1H), 3.43 (m, 1H), 3.18 (m, 1H), 3.10 (m, 1H), 2.95 (d, 1H), 2.19 (m, 1H), 2.12 (m, 1H), 2.01 (m, 2H), 1.88 (m, 1H), 1.64 (m, 1H), 1.38 (m, 1H), 1.11 (d, 3H), 0.70 (m, 1H).

Example 8

3β-(ethyl sulphonate)-2aβ,3-dihydrogaliellalactone sodium

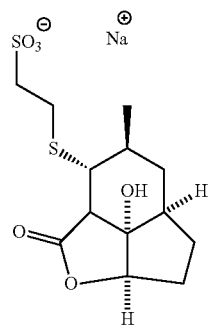

Purified by extraction.

Yield: quantitative

¹H NMR (CD₃OD) δ 4.52 (m, 1H), 3.40 (m, 1H), 3.15 (m, 2H), 3.03 (d, 1H), 3.01 (m, 2H), 2.20 (m, 1H), 2.11 (m, 1H), 1.98 (m, 2H), 1.92 (m, 1H), 1.63 (m, 1H), 1.14 (d, 3H), 0.64 (m, 1H).

Example 9

3β-(glutathione)-2aβ,3-dihydrogaliellalactone

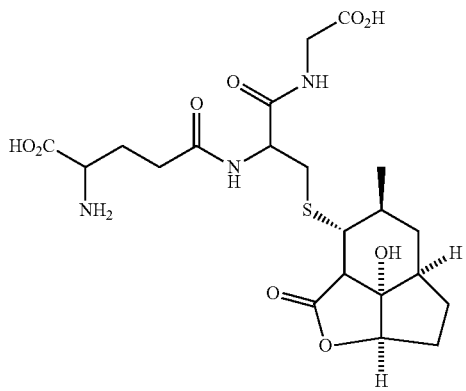

Sephadex with MeOH/H₂O 9:1, then flashed with CHCl₃/MeOH 1:1+3% acetic acid

Yield: 62%

¹H NMR (CD₃OD+10% D₂O) δ 4.64 (m, 1H), 4.60 (m, 1H), 3.92 (s, 2H), 3.83 (t, 1H), 3.42 (m, 1H), 3.15 (m, 1H), 2.98 (m, 1H), 2.87 (m, 1H), 2.55 (m, 2H), 2.19 (m, 1H), 2.15 (m, 1H), 2.11 (m, 1H), 1.99 (m, 2H), 1.92 (m, 1H), 1.65 (m, 1H), 1.27 (m, 1H), 1.22 (d, 3H), 0.62 (m, 1H).

Example 10

3β-(N-acetyl L-cysteine i-propyl ester)-2aβ,3-dihydrogaliellalactone

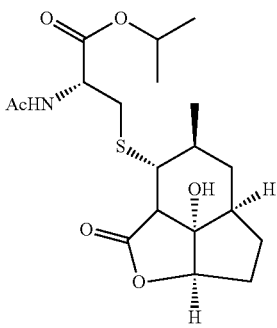

(EtOAc 100%)

Yield: 11%

¹H NMR (CDCl₃) δ 6.52 (d, 1H), 5.09 (m 1H), 4.81 (m, 1H), 4.59 (m 1H), 3.45 (m, 1H), 3.07 (m, 2H), 3.04 (m, 1H), 2.21 (m, 1H), 2.08 (s, 3H), 2.05 (m, 1H), 2.02 (m, 2H), 1.85 (m, 1H), 1.59 (m, 1H), 1.42 (m, 1H), 1.31 (d, 3H), 1.30 (d, 3H), 1.13 (d, 3H), 0.74 (m, 1H).

Example 11

3β-(N-acetyl L-cysteine methyl ester)-2aβ,3-dihydro-7-phenyl-galiellalactone

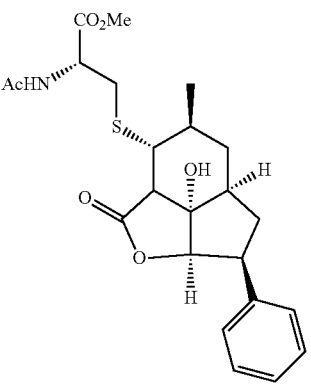

¹H NMR (CDCl₃) δ 7.33 (m, 2H), 7.31 (m, 2H), 7.25 (m, 1H), 6.62 (d, 1H), 4.88 (m, 1H), 4.64 (d, 1H), 3.79 (s, 3H), 3.53 (m, 1H), 3.53 (m, 1H), 3.12 (m, 1H), 3.07 (m, 1H), 3.01 (m, 1H), 2.54 (m, 1H), 2.26 (m, 1H), 2.09 (s, 3H), 1.99 (m, 1H), 1.69 (m, 1H), 1.61 (1H, m), 1.17 (d, 3H), 0.82 (m, 1H).

Example 12

3β-(N-acetyl-L-homocysteine methyl ester)-2aβ,3-dihydrogaliellalactone

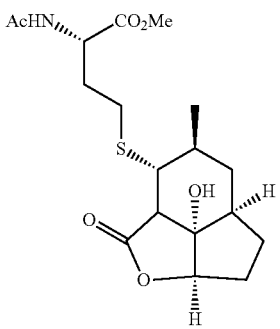

30 mg galiellalactone (0.154 mmol) was dissolved in 3 ml MeOH. 25 mg homo-cysteine (0.17 mmol) was added followed by 2 μl TEA (0.015 mmol). The reaction mixture was stirred over night at room temperature. The volatiles were removed under reduced pressure. The crude product was dissolved in 5 ml CH2Cl2 and 27 μl TEA (0.289 mmol) was added. The solution was stirred for 15 min and then cooled to 0° C. 17 μl acetyl chloride (0.238 mmol) was added and the reaction mixture was stirred at 0° C. for 2.5 h. The volatiles were removed under reduced pressure and the crude was dissolved in 2 ml MeOH. The solution was cooled to 0° C. and then 30 μl thionyl chloride was added. The reaction mixture was stirred at room temperature over night. The volatiles were removed under reduced pressure and flash chromatography (100% EtOAc) afforded 24 mg (40%) of the title compound.

¹H NMR (CD₂Cl₂) δ 6.47 (d, 1H), 4.68 (m, 1H), 4.55 (m, 1H), 3.74 (s, 3H), 3.41 (m, 1H), 2.96 (m, 1H), 2.71 (m, 2H), 2.18 (m, 1H), 2.17 (m, 2H), 2.10 (m, 2H), 2.07 (m, 2H), 2.00 (s, 3H), 1.98 (m, 2H), 1.87 (m, 1H), 1.67 (m, 1H), 1.36 (m, 1H), 1.13 (d, 3H), 0.69 (m, 1H).

HRMS: calc for C18H27NO6SNa (M+Na) 408.1457. found 408.1454.

Scheme 5

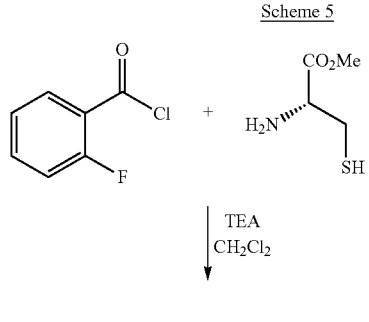

| TEA
| CH2Cl2

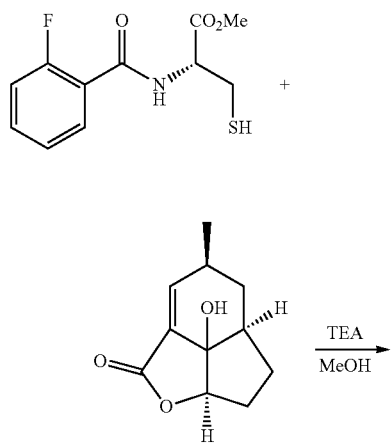

N-(2-fluorobenzoyl)-L-cysteine methyl ester 300 mg L-cysteine methyl ester hydrochloride (1.74 mmol) is dissolved in 20 ml CH2Cl2. 0.25 ml TEA (2.61 mmol) is added under N2 and then the solution is cooled to 0° C. followed by addition of 0.23 ml 2-fluorobenzoyl chloride (1.92 mmol). The reaction mixture is stirred over night and then NaHCO3 (sat.) is added and the resulting mixture is extracted three times with EtOAc. The combined organic phases are fried (Na2SO4) and the volatiles are removed under reduced pressure. The crude product is used directly in the next step.

Example 13

3β-(N-(2-fluorobenzoyl)-L-cysteine methyl ester)-2aβ,3-dihydrogaliellalactone

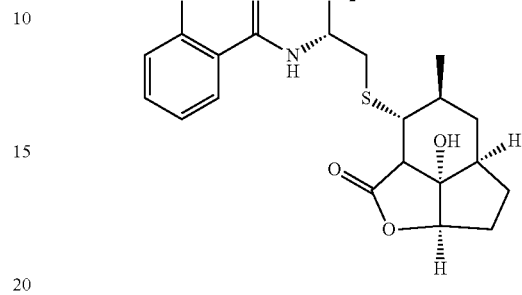

20 mg galiellalactone (0.103 mmol) was dissolved in 2 ml MeOH. 60 mg N-(2-fluorobenzoyl)-L-cysteine methyl ester (0.257 mmol) was added followed by 2 μl TEA (0.015 mmol). The reaction mixture was stirred over night at room temperature. The volatiles were removed under reduced pressure and flash chromatography (heptane/EtOAc 7:3) afforded 31 mg (67%) of the title compound.

¹H NMR (CDCl₃) δ 8.04 (m, 1H), 7.64 (d, 1H), 7.51 (m, 1H), 7.27 (m, 1H), 7.15 (m, 1H), 5.09 (m, 1H), 4.57 (m, 1H), 3.84 (s, 3H), 3.45 (m, 1H), 3.21 (m, 2H), 3.03 (m, 1H), 2.19 (m, 1H), 2.09 (m, 1H), 2.02 (m, 2H), 1.81 (m, 1H), 1.58 (m, 1H), 1.41 (m, 1H), 1.11 (d, 3H), 0.72 (m, 1H).

HRMS: calc for C22H27FNO6S (M+H) 452.1543. found 452.1520.

Scheme 6

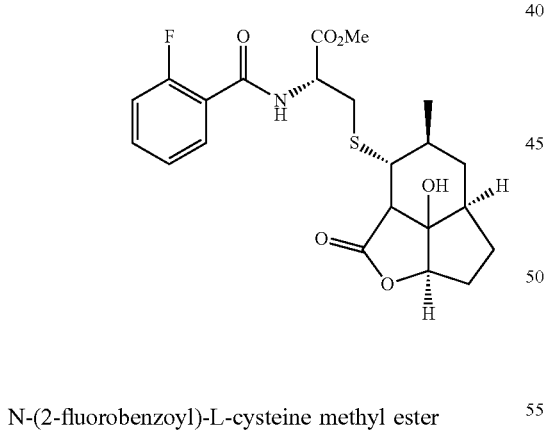

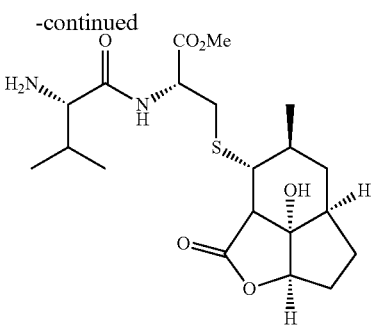

3β-(N—(N-Boc-L-valine)-L-cysteine methyl ester)-2aβ,3-dihydrogaliellalactone

A solution of 138 mg N-Boc-valine-cysteine (0.411 mmol) in 1.5 ml MeOH is added to a solution of 20 mg galiellalactone (0.103 mmol) in 1.5 ml MeOH followed by 4 µl TEA (0.03 mmol). The reaction mixture is stirred over night and then the volatiles are removed under reduced pressure. The crude is purified by flash chromatography (heptane/EtOAc 7:3) to give 32 mg of the Boc-protected title compound.

Example 14

3β-(N-(L-valine)-L-cysteine methyl ester)-2aβ,3-dihydrogaliellalactone

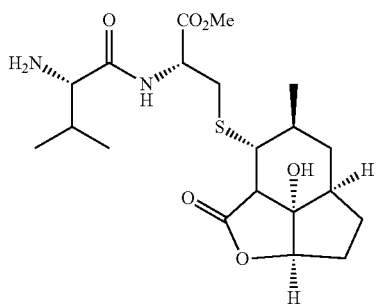

56 mg 3β-(N—(N-Boc-L-valine)-L-cysteine methyl ester)-2aβ,3-dihydrogaliellalactone (0.182 mmol) is dissolved in 3 ml diethyl ether. 4 ml 1M HCl in dietehyl ether is slowly added. After 24 h the volatiles are removed and the remains are dissolved in CH2Cl2/Et2O 1:1. The solution is cooled with an ice bath and the formed precipitate is collected by filtration. The filtrate is purified by flash chromatography (CH2Cl2 10% MeOH) to yield 30 mg (74%) of the title product.

HRMS: calc for C20H33N2OS (M+H) 429.2059. found 429.2067.

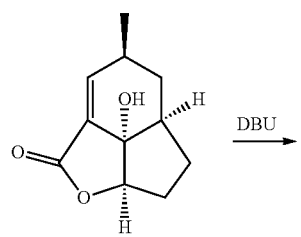

DBU →

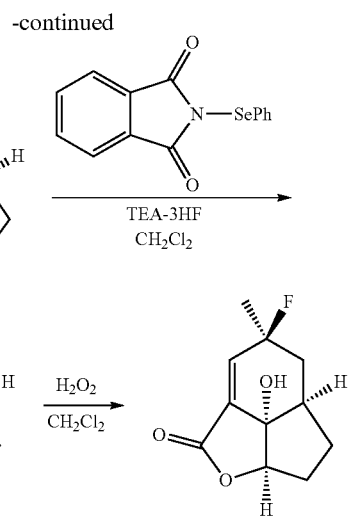

Example 15

4α-fluoro-galiellalactone

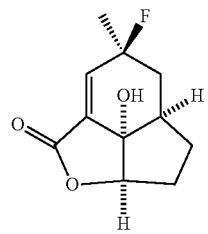

Iso-galiellalactone 1.6 g (10.30 mmol) 1,8-Diazabicyclo[5.4.0]undec-7-ene (DBU) was added to a solution of 500 mg (2.57 mmol) galiellalactone in CH$_2$Cl$_2$ and stirred overnight at room temperature. Purification with flash chromatography (heptane/EtOAc 7:3), afforded 450 mg of iso-galiellalactone. (90%)

$^1$H NMR (CDCl$_3$) δ 5.05 (m, 1H), 4.78 (m, 1H), 3.19 (s, 1H), 2.85 (m, 1H), 2.37 (m, 1H), 2.21 (m, 1H), 1.95 (m, 1H), 1.90 (m, 1H), 1.90 (m, 1H), 1.76 (s, 1H), 1.65 (m, 1H), 1.42 (m, 1H)

4α-fluoro-galiellalactone

Iso-galiellalactone was dissolved in CH$_2$Cl$_2$ and 1.5 mmol (1.5 eq) N-phenyl selenyl phthalimide was added followed by 6 mmol (6 eq) TEA-3HF. The reaction mixture was stirred at room temperature overnight diluted with diethyl ether and washed with NaHCO$_3$ (aq). The organic phase was dried and concentrated under reduced pressure.

To a solution of resulting crude selenylated product (38 mg, 0.1 mmol) in 2 ml of CH$_2$Cl2 was added H$_2$O$_2$ (12 uL) at 0° C. under N$_2$, and stirred for 3 h. The reaction was quenched by 2 ml NaHCO$_3$ sat at 0° C. and extracted with CH$_2$Cl$_2$ (5 ml×3), dried with MgSO$_4$ and concentrated under reduced pressure. Purification with flash chromatography (heptane/EtOAc 7:3), afforded 16 mg of the 4α-fluoro-galiellalactone. (65%)

$^1$H NMR (CDCl$_3$) δ 6.91 (d, 1H), 4.86 (d, 1H), 2.42 (m, 1H), 2.29 (m, 1H), 2.19 (m, 1H), 2.14 (m, 1H), 1.80 (m, 1H), 1.75 (m, 1H), 1.61 (d, 3H), 1.60 (m, 1H)

Example 16

4α-fluoro-3β-(N-acetyl L-cysteine methyl ester)-2aβ,3-dihydrogaliellalactone

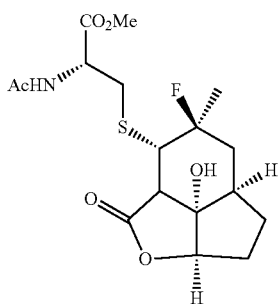

15 mg 4α-fluoro-galiellalactone (0.071 mmol) was dissolved in 2 ml MeOH. 14 mg N-acetyl-L-cysteine methyl ester (0.078 mmol) was added followed by 2 µl TEA (0.015 mmol). The reaction mixture was stirred over night at room temperature. The volatiles were removed under reduced pressure and flash chromatography (heptane/EtOAc 7:3) afforded 12 mg (43%) of the title compound.

$^1$H NMR (CDCl$_3$) δ 6.64, (d, 1H), 4.90 (m, 1H), 4.65 (m, 1H), 3.47 (m, 1H), 3.43 (m, 1H), 3.21 (m, 1H), 3.12 (m, 1H), 2.24 (m, 1H), 2.07 (s, 3H), 2.05 (m, 1H), 1.96 (m, 1H), 1.90 (m, 1H) 1.83 (m, 1H), 1.81 (m, 1H), 1.80 (m, 1H), 1.57 (s, 3H)

BIOLOGICAL EXAMPLES

Biological Example

The usefulness of the compounds, as defined in the embodiments herein, as prodrugs to enhance the plasma exposure of tricyclic compounds that may be used treating, revoking, mitigating, alleviating and/or preventing different forms of cancer, were evaluated in an in vivo pharmacokinetic (PK) study in mice.

Example 17 Pharmacokinetic (PK) Study

Doses of the test items were prepared at a drug concentration of 0.5 mg/mL in 5% DMSO in 50 mM citrate buffer (citric acid/sodium citrate), pH 4.0.

Oral doses were administered in a volume of 20 mL/kg (10 mg/kg) to groups of 24 mice and blood samples taken, under terminal barbiturate anaesthesia, at eight time-points out to 8 hours post-dose (n=3 mice per time-point).

Blood samples were transferred to tubes containing EDTA as anticoagulant and, as soon as practicable after collection, samples were centrifuged to yield plasma which was immediately frozen awaiting analysis. Following blood collection, brains were removed from all animals for possible future analysis and immediately frozen by immersion in liquid nitrogen. All samples were analyzed using LC-MS/MS.

Plasma Sample Analysis

Plasma proteins were precipitated and compounds extracted by the addition of three volumes of acetonitrile containing analytical internal standard (reserpine). Samples were centrifuged for 30 minutes at 3452 g in a Sorvall bench centrifuge and the supernatant fractions removed for MS analysis.

Quantification of the active compound e.g. galiellalactone, was by extrapolation from calibration lines prepared in control mouse plasma and analyzed concurrently with experimental samples and Quality Control (QC) samples prepared in control mouse plasma. If the compounds were instable in mouse plasma, calibration lines were constructed in water for qualitative MS comparison with any signal seen in plasma samples.

Pharmacokinetic Analysis

Pharmacokinetic parameters of the test items were determined using the mean data from the n=3 mice at each time-point. Non-compartmental analysis was performed using the software package PK Solutions 2.0 from Summit Research Services. AUC values were calculated by the trapezoidal method.

Definition of Terms

AUC 0-t: Area under the plasma drug concentration/time curve from 0 minutes to last quantifiable data point AUC 0-∞: Area under the curve from 0 minutes extrapolated to infinity GL: Galiellalactone

TABLE 1

Pharmacokinectic parameters of examples

| Compound | AUC 0-t (µg GL/mL·min) | AUC 0-∞ (µg GL/mL·min) |
| --- | --- | --- |
| Galiellalactone (control) | 5 | 6 |
| Example 1 | 85 | 102 |
| Example 2 | 36 | 41 |
| Example 4 | 20 | 22 |
| Example 5 | 15 | 21 |
| Example 13 | 7.8 | 11 |
| Example 6 | 11 | 17 |
| Example 12 | 150 | 155 |
| Example 14 | 97 | 101 |
| Example 3 | 117 | 120 |
| HCl 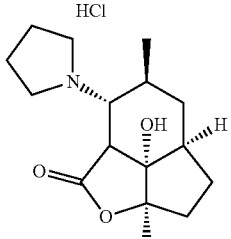 (negative control) | 2.2 | 2.5 |

As can be seen from table 1, oral administration of prodrug compounds defined by the claims increases the plasma exposure over time (AUC) of galiellalactone compared to oral administration of galiellalactone itself. Noteworthy is that amine adducts, as exemplified by 3β-(N-pyrrolidine)-2aβ,3-dihydrogaliellalactone, do not increase the AUC.

Example 18

Chemical Stability in Phosphate Buffered Saline

The chemical stability of test compounds was determined in 96-well plate format. Compounds in DMSO stock solutions were diluted (n=2) in the required matrix (0.1 M phosphate buffered saline) to a concentration of 10 µM (2% DMSO final) and mixed at room temperature on an orbital shaker, with aliquots removed at 2 and 4 hours for testing. DMSO, containing an analytical internal standard, was added to the aliquots, vortex-mixed and analysed immediately by LC-MS/MS. Equivalent T=0 samples were also included, with sample preparation staggered to allow sequential injections of timed aliquots and the T=0 samples.

The amount of compound remaining (expressed as %) was determined from the MS response in each sample relative to that in the T=0 samples (normalized for internal standard).

Ln plots of the % remaining were used to determine the half-life of compound disappearance from the relationship:

$t_{1/2}$ (min)=$-0.693/\lambda$, where $\lambda$ is the slope of the Ln concentration vs time curve.

TABLE 2 half-life of compound for selected compounds in PBS

| Compound | Half-life (min) 0.1M PBS pH 7.4 |
|---|---|
| [structure: CO₂Me, H₂N, S, OH, H, O] | 22 |
| [structure: CO₂H, H₂N, S, OH, H, O] | 14 |
| [structure: HCl, pyrrolidine N, OH, H, O] | 18 |
| Example 3 | >150 |
| Example 5 | >138 |
| Example 6 | >150 |

TABLE 2-continued half-life of compound for selected compounds in PBS

| Compound | Half-life (min) 0.1M PBS pH 7.4 |
|---|---|
| Example 14 | 66 |
| Example 7 | >150 |
| Example 8 | >150 |
| Example 9 | >150 |

As can be seen in table 2 the adducts of cysteine and galiellalactone and cysteine Me-ester and galiellalactone had low stability in PBS buffer (t1/2<30 min). This is comparable to the low stability of the pyrrolidine adduct 3β-(N-pyrrolidine)-2αβ,3-dihydrogaliellalactone which did not provide any improved in vivo plasma exposure of galiellalactone following oral administration (cf. Table 1). It is thus concluded that these adducts, which have low chemical stability, will not function as effective prodrugs. On the contrary, compounds defined by the claims have significantly increased chemical stability, which correlates well with their improved in vivo plasma exposure (cf. Table 1). Thus they are effective as prodrugs.

Example 19 Anti-Proliferative Activity of Example 15 (4α-Fluoro-Galiellalactone)

WST-1 Cell Proliferation Assay

The functional activity of example 15 in comparison to galiellalactone was evaluated using WST-1 proliferation assay (J. Biol. Chem. 2014, 289:15969-15978) on DU145, PC-3, LNCaP or IL-6 stimulated LNCaP. The cells were cultured in 96-well plates (2000 cells/well in 200 µl of medium) and allowed to set for 24 h. The cells were treated with 10 µM of 4α-fluoro-galiellalactone or galiellalactone for 72 h. Samples were made in triplicate. 20 µl WST-1 solution (Roche Applied Science) was added per well and incubated at 37° C. for 4 h. The absorbance of each well was measured using a scanning multi-well spectrophotometer, ELISA reader at a wavelength of 450 nm and reference wavelength of 690 nm. The results presented in Table 3 below are presented as percent of untreated control cells.

Western Blot Analysis of pSTAT3 in Prostate Cancer Cells

Samples were separated on 7.5% precast gel (Mini-PROTEAN TGX; Bio-Rad) or 8% Tris Bis self cast gels. The gels were blotted onto PVDF membranes and blocked with 5% milk or 5% BSA. Membranes were incubated with primary antibody diluted in 5% milk or 5% BSA for 1 h at room temperature or over night at 4° C. with antibodies raised against STAT3, pSTAT3 tyr-705 or pSTAT3 ser-727 (Cell Signaling Technology). After incubation with secondary anti-mouse or anti-rabbit antibody conjugated with horseradish peroxidase (GE Healthcare Life Sciences) the membrane was treated with enhanced chemiluminescent reagent (Santa Cruz Biotechnology or Millipore) followed by exposure to X-Ray film or visualized using a Chemidoc XRS system (Bio-Rad).

TABLE 3

Proliferation of pSTAT3 cell lines in the presence of galiellalactone and 4α-fluoro-galiellalactone

| | | | % Remaining Proliferation | |
|---|---|---|---|---|
| Time/dose | Cell type | pSTAT3 expression | Galiellalactone | 4α-fluoro-galiellalactone |
| 72 hours/ 10 μM | DU145 | + | 18 | 16 |
| | PC3 | − | 31 | 68 |
| | LNCaP | − | 77 | 105 |
| | LNCaP-IL6 | + | 17 | 20 |

Table 3 shows that proliferation of the pSTAT3 negative cell lines PC3 and LNCaP are less affected by 4α-fluoro-galiellalactone than galiellalactone (both at 10 μM). On the other hand, the pSTAT3 positive cells are equally sensitive to 4α-fluoro-galiellalactone and galiellalactone. This shows that 4α-fluoro-galiellalactone is significantly more selective for STAT3 than is galiellalactone.

The invention claimed is:
1. A compound according to formula (I),

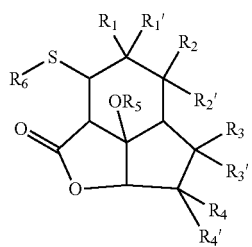

wherein
$R_1$ and $R_1'$ are independently selected from the group consisting of H, C1-5 alkyl, C1-5 fluoroalkyl, halo, C3-8 non-aromatic carbocycle, C0-5 alkyleneOC0-5 alkyl, C0-3 alkyleneOC1-5 fluoroalkyl, C0-3 alkyleneOC(O)C1-5 alkyl, OC2-3 alkyleneN(C0-5 alkyl)$_2$ in which the C0-5 alkyl may be the same or different, C0-3 alkyleneNHC0-5 alkyl, C0-3 alkyleneN(C1-5 alkyl)$_2$ in which the C1-5 alkyl may be the same or different, C0-3 alkyleneN(C0-5 alkyl)C(O)C1-5 alkyl, C0-3 alkyleneNHaryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C0-3 alkyleneNHheteroaryl, wherein said heteroaryl is a 5- or 6-membered heteroaryl, said heteroaryl being unsubstituted or substituted with a one or several independently selected C1-5 alkyl groups, C0-3 alkyleneC(O)NHC0-5 alkyl, C0-3 alkyleneC(O)N(C1-5 alkyl)$_2$ in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C0-3 alkylene heteroaryl, wherein said heteroaryl is a 5- or 6-membered heteroaryl, said heteroaryl being unsubstituted or substituted with a one or several independently selected C1-5 alkyl groups, halo, C0-1 alkylene cyano, SC0-5 alkyl, C0-3 alkyleneSO$_2$C0-5 alkyl, nitro, C(O)C0-C5 alkyl, C(O)C1-C5 fluoroalkyl, N(C0-C3 alkyl)SO$_2$C1-C5 alkyl, and N(C0-C5 alkyl)SO$_2$C1-5 fluoroalkyl;

$R_2$ and $R_2'$ are independently selected from the group consisting of H, C1-5 alkyl, C1-5 fluoroalkyl, halo, C3-8 non-aromatic carbocycle, C0-5 alkyleneOC0-5 alkyl, C0-3 alkyleneOC1-5 fluoroalkyl, C0-3 alkyleneOC(O)C1-5 alkyl, OC2-3 alkyleneN(C0-5 alkyl)$_2$ in which the C0-5 alkyl may be the same or different, C0-3 alkyleneNHC0-5 alkyl, C0-3 alkyleneN(C1-5 alkyl)$_2$ in which the C1-5 alkyl may be the same or different, C0-3 alkyleneN(C0-5 alkyl)C(O)C1-5 alkyl, C0-3 alkyleneNHaryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C0-3 alkyleneNHheteroaryl, wherein said heteroaryl is a 5- or 6-membered heteroaryl, said heteroaryl being unsubstituted or substituted with a one or several independently selected C1-5 alkyl groups, C0-3 alkyleneC(O)NHC0-5 alkyl, C0-3 alkyleneC(O)N(C1-5 alkyl)$_2$ in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C0-3 alkylene heteroaryl, wherein said heteroaryl is a 5- or 6-membered heteroaryl, said heteroaryl being unsubstituted or substituted with a one or several independently selected C1-5 alkyl groups, halo, C0-1 alkylene cyano, SC0-5 alkyl, C0-3 alkyleneSO$_2$C0-5 alkyl, nitro, C(O)C0-C5 alkyl, C(O)C1-C5 fluoroalkyl, N(C0-C3 alkyl)SO$_2$C1-C5 alkyl, and N(C0-C5 alkyl)SO$_2$C1-5 fluoroalkyl;

$R_3$ and $R_3'$ are independently selected from the group consisting of H, C1-5 alkyl, C1-5 fluoroalkyl, halo, C3-8 non-aromatic carbocycle, C0-5 alkyleneOC0-5 alkyl, C0-3 alkyleneOC1-5 fluoroalkyl, C0-3 alkyleneOC(O)C1-5 alkyl, OC2-3 alkyleneN(C0-5 alkyl)$_2$ in which the C0-5 alkyl may be the same or different, C0-3 alkyleneNHC0-5 alkyl, C0-3 alkyleneN(C1-5 alkyl)$_2$ in which the C1-5 alkyl may be the same or different, C0-3 alkyleneN(C0-5 alkyl)C(O)C1-5 alkyl, C0-3 alkyleneNHaryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C0-3 alkyleneNHheteroaryl, wherein said heteroaryl is a 5- or 6-membered heteroaryl, said heteroaryl being unsubstituted or substituted with a one or several independently selected C1-5 alkyl groups, C0-3 alkyleneC(O)NHC0-5 alkyl, C0-3 alkyleneC(O)N(C1-5 alkyl)$_2$ in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C0-3 alkylene heteroaryl, wherein said heteroaryl is a 5- or 6-membered heteroaryl, said heteroaryl being unsubstituted or substituted with a one or several independently selected C1-5 alkyl groups, halo, C0-1 alkylene cyano, SC0-5 alkyl, C0-3 alkyleneSO$_2$C0-5 alkyl, nitro, C(O)C0-C5 alkyl, C(O)C1-C5 fluoroalkyl, N(C0-C3 alkyl)SO$_2$C1-C5 alkyl, and N(C0-C5 alkyl)SO$_2$C1-5 fluoroalkyl;

$R_4$ and $R_4'$ are independently selected from the group consisting of H, C1-5 alkyl, C1-5 fluoroalkyl, halo, C3-8 non-aromatic carbocycle, C0-5 alkyleneOC0-5 alkyl, C0-3 alkyleneOC1-5 fluoroalkyl, C0-3 alkyleneOC(O)C1-5 alkyl, OC2-3 alkyleneN(C0-5 alkyl)$_2$ in which the C0-5 alkyl may be the same or different, C0-3 alkyleneNHC0-5 alkyl, C0-3 alkyleneN(C1-5 alkyl)$_2$ in which the C1-5 alkyl may be the same or different, C0-3 alkyleneN(C0-5 alkyl)C(O)C1-5 alkyl, C0-3 alkyleneNHaryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C0-3 alkyleneNHheteroaryl, wherein said heteroaryl is a 5- or 6-membered heteroaryl, said heteroaryl being unsubstituted or substituted with a one or several independently selected C1-5 alkyl groups, C0-3 alkyleneC(O)NHC0-5 alkyl, C0-3 alkyleneC(O)N(C1-5 alkyl)$_2$ in which the C1-5 alkyl may be the same or different, C0-3 alkyleneC(O)N(C4-5 alkylene), C0-3 alkyleneC(O)OC0-5 alkyl, a 3- to 8-membered non-aromatic heterocycle, C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C0-3 alkylene heteroaryl, wherein said heteroaryl is a 5- or 6-membered heteroaryl, said heteroaryl being unsubstituted or substituted with a one or several independently selected C1-5 alkyl groups, halo, C0-1 alkylene cyano, SC0-5 alkyl, C0-3 alkyleneSO$_2$C0-5 alkyl, nitro, C(O)C0-C5 alkyl, C(O)C1-C5 fluoroalkyl, N(C0-C3 alkyl)SO$_2$C1-C5 alkyl, and N(C0-C5 alkyl)SO$_2$C1-5 fluoroalkyl;

$R_5$ is selected from the group consisting of H, C1-5 alkyl, C1-5 fluoroalkyl, C(O)C1-5 alkyl, C2-3 alkyleneN(C0-5 alkyl)$_2$ in which the C0-5 alkyl may be the same or different, C(O)N(0-5 alkyl)$_2$ in which the C0-5 alkyl may be the same or different, C(O)aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C(O)heteroaryl, wherein said heteroaryl is a 5- or 6-membered heteroaryl, said heteroaryl being unsubstituted or substituted with a one or several independently selected C1-5 alkyl groups, C(O)C1-C3alkylenearyl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, and C(O)C1-C3alkyleneheteroaryl, wherein said heteroaryl is a 5- or 6-membered heteroaryl, said heteroaryl being unsubstituted or substituted with a one or several independently selected C1-5 alkyl groups; and $R_6$ is a moiety according to formula (II),

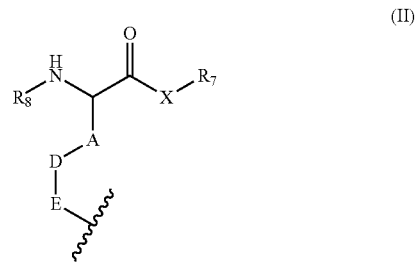

(II)

wherein the waved line indicates the point of attachment to the sulfur atom in formula (I);

A is a C1-5 alkylene;

D is a bond, a phenylene, or a heteroarylene, wherein said heteroarylene is a 5- or 6-membered heteroarylene;

E is a bond or a C1-5 alkylene;

X is NC0-C5 alkyl or "O" (oxygen);

R7 is selected from the group consisting of H, provided that X is NC0-C5 alkyl, R7 is not to be H if X is "O" (oxygen), C1-C10 alkyl, C1-5 alkyleneN(C1-5 alkyl)$_2$ in which the C1-5 alkyl may be the same or different, C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)$_2$ in which the C0-5 alkyl may be the same or different, C1-3 alkylene heteroaryl, wherein said heteroaryl is a 5- or 6-membered heteroaryl, said heteroaryl being unsubstituted or substituted with a one or several independently selected C1-5 alkyl groups, an amino acid residue selected from the group consisting alanine, arginine, asparagine, aspartic acid, cysteine, glutamine, glutamic acid, glycine, histidine, isoleucine, leucine, lysine; methionine, phenylalanine, proline, threonine, tryptophan, tyrosine and valine, which amino acid residue is connected to the moiety according to formula (II) at the N-terminal of the amino acid residue and optionally esterfied at the C-terminal with a C1-5 monohydric alkanol, and a di-, a tri-, or a tetrapeptide residue, wherein the amino acid residues in said peptide residue are independently selected from the group consisting alanine, arginine, asparagine, aspartic acid, cysteine, glutamine, glutamic acid, glycine, histidine, isoleucine, leucine, lysine; methionine, phenylalanine, proline, threonine, tryptophan, tyrosine and valine, the peptide residue being connected to the moiety according to formula (II) at the N-terminal of the peptide and optionally esterfied at the C-terminal with a C1-5 monohydric alkanol; and R8 is selected from the group consisting of C(O)C1-C6 alkyl, C(O)OC1-C6 alkyl, C(O)C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)₂ in which the C0-5 alkyl may be the same or different, C(O)C0-3 alkylene heteroaryl, wherein said heteroaryl is a 5- or 6-membered heteroaryl, said heteroaryl being unsubstituted or substituted with a one or several independently selected C1-5 alkyl groups, an amino acid residue selected from the group consisting alanine, arginine, asparagine, aspartic acid, cysteine, glutamine, glutamic acid, glycine, histidine, isoleucine, leucine, lysine; methionine, phenylalanine, proline, threonine, tryptophan, tyrosine and valine, which amino acid residue is connected to the moiety according to formula (II) at the C-terminal of the amino acid residue, and which amino acid residue optionally is N-acylated, wherein said acyl group is selected from the group consisting C(O)C1-C6 alkyl, and C(O)C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)₂ in which the C0-5 alkyl may be the same or different, and a di-, a tri-, or a tetrapeptide residue, wherein the amino acid residues in said peptide residue are independently selected from the group consisting alanine, arginine, asparagine, aspartic acid, cysteine, glutamine, glutamic acid, glycine, histidine, isoleucine, leucine, lysine; methionine, phenylalanine, proline, threonine, tryptophan, tyrosine and valine, the peptide residue being connected to the moiety according to formula (II) at the C-terminal of the peptide, and the N-terminal of the peptide optionally being N-acelyated, wherein said acyl group is selected from the group consisting C(O)C1-C6 alkyl and C(O)C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)₂ in which the C0-5 alkyl may be the same or different;

as a free base, an acid in its non-charged protonated form, a pharmaceutically acceptable addition salt, solvate, solvate of a salt thereof, a pure diastereomer, a pure enantiomer, a diastereomeric mixture, a racemic mixture, a scalemic mixture, a corresponding tautomeric form resulting from a hydrogen shift between two hetero-atoms and/or the corresponding tautomeric form resulting from a keto-enol tautomerization.

2. The compound according to claim 1, wherein the compound has the relative or absolute stereochemistry according to formula (III),

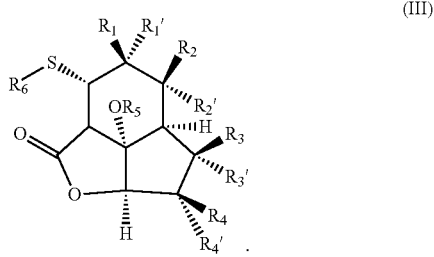

(III)

3. The compound according to claim 1, wherein $R_1$, $R_1'$, $R_2$, $R_2'$, $R_3$, $R_3'$, $R_4$ and $R_4'$ are independently selected from the group consisting of H, C1-5 alkyl, halo, aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)₂ in which the C0-5 alkyl may be the same or different, CH₂aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)₂ in which the C0-5 alkyl may be the same or different, heteroaryl, wherein said heteroaryl is a 5- or 6-membered heteroaryl, said heteroaryl being unsubstituted or substituted with a one or several independently selected C1-5 alkyl groups, and CH₂heteroaryl, wherein said heteroaryl is a 5- or 6-membered heteroaryl, said heteroaryl being unsubstituted or substituted with a one or several independently selected C1-5 alkyl groups.

4. The compound according claim 1, wherein $R_1$ is methyl; $R_1'$ is hydrogen; $R_2$, $R_2'$, $R_3$, and $R_3'$ are all hydrogen; and $R_4$ and $R_4'$ are independently selected from the group consisting of H and phenyl.

5. The compound according claim 1, wherein $R_1$ is halo; $R_1'$ is methyl; $R_2$, $R_2'$, $R_3$, and $R_3'$ are all hydrogen; and $R_4$ and $R_4'$ are independently selected from the group consisting of H and phenyl.

6. The compound according to claim 5, wherein $R_1$ is fluorine; $R_4$ is H; $R_4'$ is hydrogen; and $R_5$ is H.

7. The compound according to claim 4, wherein $R_4$ is H; $R_4'$ is hydrogen; and $R_5$ is H.

8. The compound according to claim 1, wherein

D is a bond or a phenylene;

$R_7$ is selected from the group consisting of H, provided that X is NC0-C5 alkyl, R7 is not to be H if X is "O" (oxygen), C1-C10 alkyl, and C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)₂ in which the C0-5 alkyl may be the same or different; and $R_8$ is selected from the group consisting of C(O)C1-C6 alkyl, C(O)C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano, and N(C0-5 alkyl)₂ in which the C0-5 alkyl may be the same or different, and an amino acid residue selected from the group consisting alanine, glycine, isoleucine, leucine, lysine, methionine, phenylalanine, tyrosine and valine, which amino acid residue is connected to the moiety according to formula (II) at the C-terminal of the amino acid residue.

9. The compound according to claim 8, wherein $R_6$ is a moiety according to formula (IV),

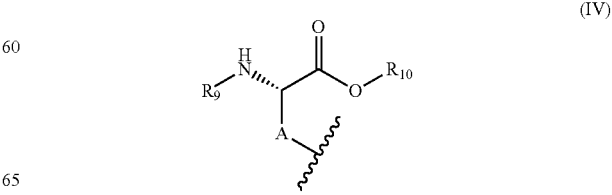

(IV)

wherein the waved line indicates the point of attachment to the sulfur atom in formula (I);

A is a C1-5 alkylene;

R₉ is selected from the group consisting of C(O)C1-C6 alkyl, C(O)C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)₂ in which the C0-5 alkyl may be the same or different, and an amino acid residue selected from the group consisting alanine, glycine, isoleucine, leucine, lysine; methionine, phenylalanine, tyrosine and valine, which amino acid residue is connected to the moiety according to formula (IV) at the C-terminal of the amino acid residue; and R₁₀ is selected from the group consisting of C1-C10 alkyl and C0-3 alkylene aryl, wherein the aryl is unsubstituted or substituted with a one or several substituents independently selected from the group consisting of C1-5 alkyl, C1-5 fluoroalkyl, halo, C0-5 alkyleneOC0-5 alkyl, nitro, cyano and N(C0-5 alkyl)₂ in which the C0-5 alkyl may be the same or different.

10. The compound according to claim 1, wherein said compound is a compound according to formula (V),

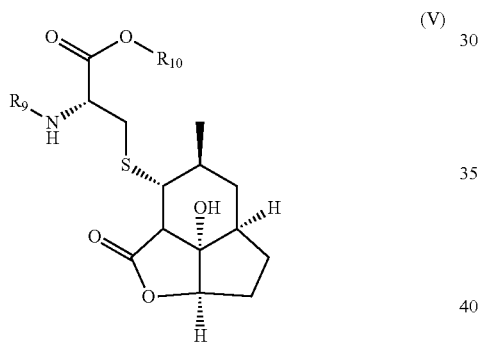

(V)

wherein R₉ is selected from the group consisting of C(O)C1-C5 alkyl, C(O)C0-3 alkylene aryl, wherein the aryl is unsubstituted or substituted with a one or several substituents independently selected from the group consisting of fluorine, chlorine and bromine, and an amino acid residue selected from the group consisting alanine, glycine, isoleucine, leucine, lysine and valine, which amino acid residue is connected to the moiety according to formula (IV) at the C-terminal of the amino acid residue; and R₁₀ is selected from the group consisting of C1-C6 alkyl and C1-3 alkylene aryl, wherein the aryl is unsubstituted or substituted with a one or several substituents independently selected from the group consisting of fluorine, chlorine and bromine.

11. A pharmaceutical composition comprising a compound according to claim 1 and at least one pharmaceutically acceptable carrier or excipient.

12. The pharmaceutical composition according to claim 11, wherein said composition further comprises at least one additional therapeutic agent.

13. The compound according to claim 1, wherein said compound is selected from the group consisting of:

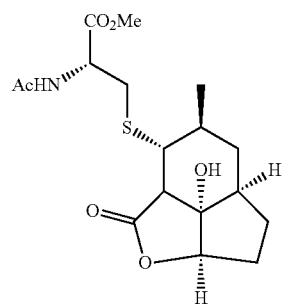

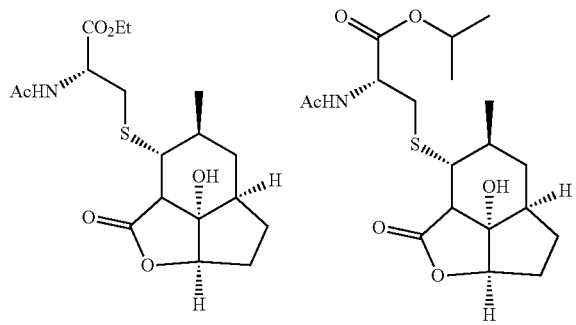

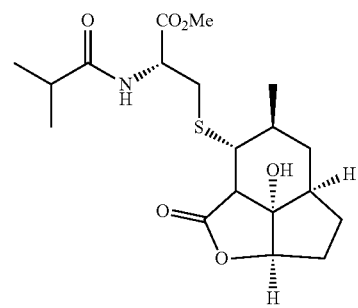

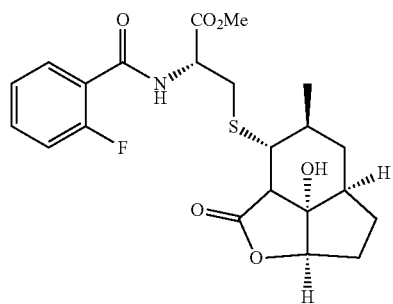

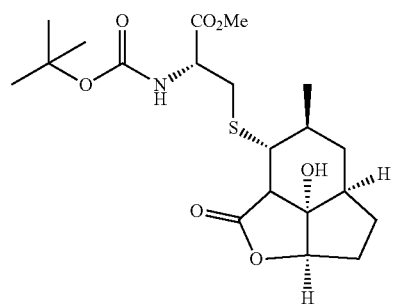

-continued
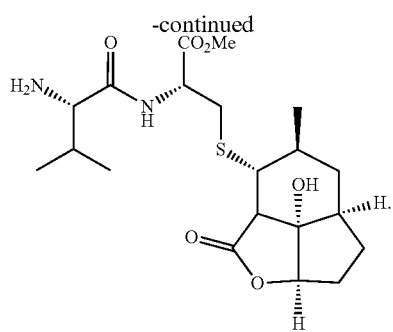
15. The method of claim 11, wherein the compound is selected from the group consisting of:
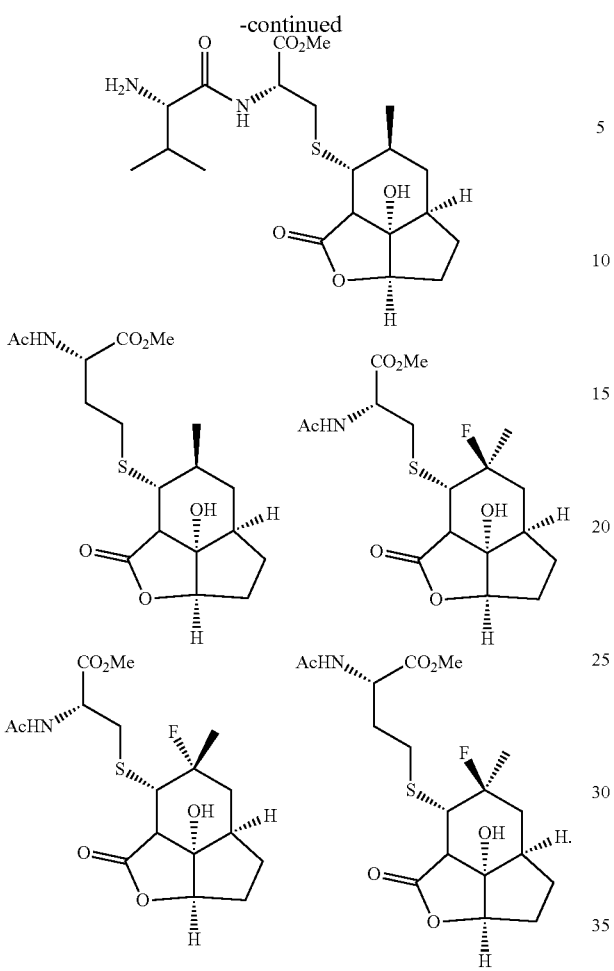
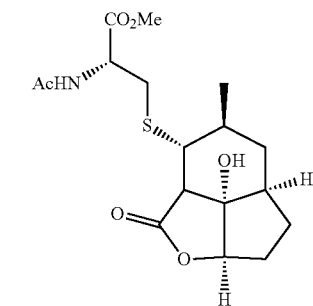
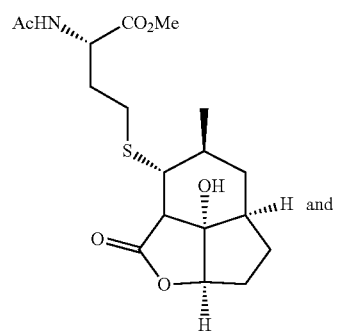
14. The compound according to claim 1, wherein said compound is selected from the group consisting of:
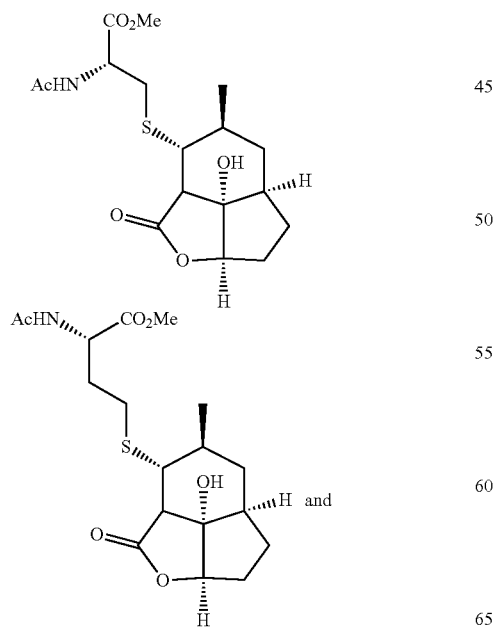
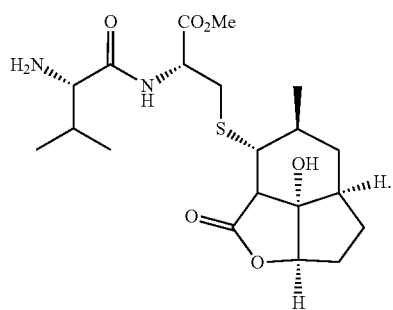
* * * * *